(12) United States Patent
He et al.

(10) Patent No.: US 8,362,050 B2
(45) Date of Patent: Jan. 29, 2013

(54) COMPOUNDS AND METHODS FOR MODULATING G PROTEIN-COUPLED RECEPTORS

(75) Inventors: Xiaohui He, San Diego, CA (US); Xuefeng Zhu, San Diego, CA (US); Kunyong Yang, San Diego, CA (US); Robert Epple, San Diego, CA (US); Hong Liu, San Diego, CA (US)

(73) Assignee: IRM LLC, Hamilton (BM)

( * ) Notice: Subject to any disclaimer, the term of this patent is extended or adjusted under 35 U.S.C. 154(b) by 81 days.

(21) Appl. No.: 12/999,887

(22) PCT Filed: Jun. 23, 2009

(86) PCT No.: PCT/US2009/048265
§ 371 (c)(1), (2), (4) Date: Mar. 25, 2011

(87) PCT Pub. No.: WO2010/008831
PCT Pub. Date: Jan. 21, 2010

(65) Prior Publication Data
US 2011/0172278 A1    Jul. 14, 2011

Related U.S. Application Data

(60) Provisional application No. 61/075,094, filed on Jun. 24, 2008.

(51) Int. Cl.
*A61K 31/426* (2006.01)
*C07D 277/18* (2006.01)

(52) U.S. Cl. ..................................... 514/370; 548/190

(58) Field of Classification Search ............... 514/370; 548/190
See application file for complete search history.

(56) References Cited

U.S. PATENT DOCUMENTS

| | | |
|---|---|---|
| 2008/0167378 A1 | 7/2008 | Fukatsu et al. |
| 2010/0022592 A1 | 1/2010 | Epple et al. |
| 2010/0035944 A1 | 2/2010 | Epple et al. |
| 2010/0130559 A1 | 5/2010 | Hashimoto et al. |
| 2010/0190831 A1 | 7/2010 | Shi et al. |
| 2010/0274022 A1 | 10/2010 | Tsujimoto et al. |
| 2011/0065739 A1 | 3/2011 | Ishikawa et al. |
| 2011/0184031 A1 | 7/2011 | Tsujimoto et al. |

FOREIGN PATENT DOCUMENTS

| | | |
|---|---|---|
| JP | 2008001690 | 1/2008 |
| JP | 2008195625 | 8/2008 |
| WO | WO03062215 | 7/2003 |
| WO | WO2004110350 | 12/2004 |
| WO | WO2006044456 | 4/2006 |
| WO | WO2006122011 | 11/2006 |

OTHER PUBLICATIONS

Nanda, et al., Journal of the Indian Chemical Society (1972), 49(3), p. 251-4 (Abstract from STN search report).*

* cited by examiner

*Primary Examiner* — Yong Chu
(74) *Attorney, Agent, or Firm* — Daniel E. Raymond; Genomics Institute of the Novartis Research Foundation

(57) ABSTRACT

The invention provides compounds, pharmaceutical compositions comprising such compounds and methods of using such compounds to treat or prevent diseases or disorders associated with or mediated by G protein-coupled receptors, in particular G protein-coupled receptor 120.

11 Claims, No Drawings

COMPOUNDS AND METHODS FOR MODULATING G PROTEIN-COUPLED RECEPTORS

CROSS-REFERENCE TO RELATED APPLICATIONS

This application is a 371 U.S. national phase application of international application number PCT/US2009/048265 filed 23 Jun. 2009, which application claims the benefit of priority under 35 U.S.C. §119(e) to U.S. Provisional Patent Application No. 61/075,094, filed Jun. 24, 2008. The disclosure of these applications is incorporated herein by reference in their entirety and for all purposes.

FIELD OF THE INVENTION

The invention relates to compounds, pharmaceutical compositions comprising such compounds and methods of using such compounds to treat or prevent diseases or disorders associated with or mediated by G protein-coupled receptors.

BACKGROUND OF THE INVENTION

G-protein coupled receptors (GPCRs) constitute a major class of proteins responsible for transducing a signal within a cell. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease. For example, specific defects in the rhodopsin gene and the V2 vasopressin receptor gene have been shown to cause various forms of retinitis pigmentosum, and nephrogenic diabetes insipidus. These receptors are important to both the central nervous system and peripheral physiological processes.

SUMMARY OF THE INVENTION

Provided herein are compounds and pharmaceutical compositions thereof, which are useful modulators of G protein-coupled receptors. In certain embodiments, such compounds and pharmaceutical compositions are useful modulators of G protein-coupled receptor 120.

In one aspect, such compounds, and the pharmaceutically acceptable salts, pharmaceutically acceptable solvates (e.g. hydrates), the N-oxide derivatives, prodrug derivatives, protected derivatives, individual isomers and mixture of isomers thereof, provided herein, have a structure according to Formula (I):

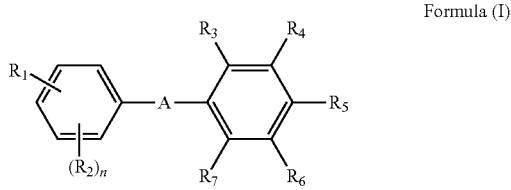

Formula (I)

wherein:

n is selected from 0, 1, 2, 3 and 4;

A is selected from:

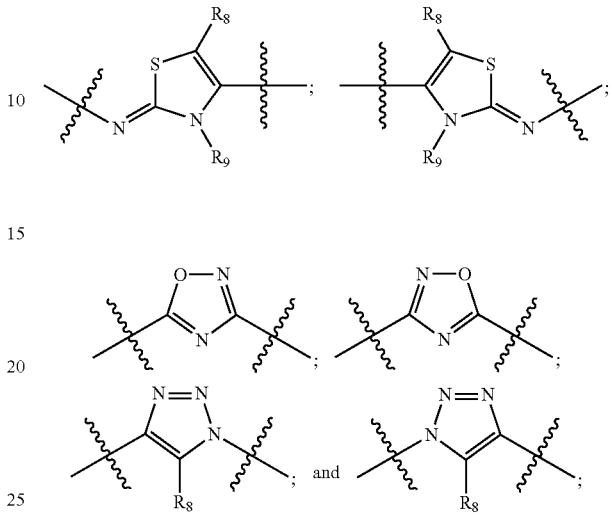

wherein:
  $R_8$ is selected from H, $C_{1-4}$alkyl and phenyl optionally substituted with 1 to 3 radicals independently selected from halo, $C_{1-4}$alkyl, halo-substituted-$C_{1-4}$alkyl, $C_{1-4}$alkoxy and halo-substituted-$C_{1-4}$alkoxy;

$R_9$ is selected from $C_{1-6}$alkyl, halo-substituted-$C_{1-4}$alkyl and —$X_1R_{10}$; wherein $X_1$ is a bond or $C_{1-4}$alkylene; $R_{10}$ is $C_{3-8}$cycloalkyl;

$R_1$ is selected from —COOH, —SO$_3$H and tetrazolyl;

$R_2$ is selected from halo, $C_{1-4}$alkyl, halo-substituted-$C_{1-4}$alkyl, $C_{1-4}$alkoxy and halo-substituted-$C_{1-4}$alkoxy;

$R_3$, $R_4$, $R_5$, $R_6$ or $R_7$ are independently selected from H, cyano, hydroxyl, nitro, halo, $C_{1-4}$alkyl, halo-substituted-$C_{1-4}$alkyl, $C_{1-4}$alkoxy, halo-substituted-$C_{1-4}$alkoxy, $X_2OR_{11}$, —$X_2NR_{12}R_{13}$, —$X_2R_{11}$, —$X_2OX_3R_{11}$ and —$X_2OX_3OR_{11}$; wherein $X_2$ is selected from a bond and $C_{1-4}$alkylene; $X_3$ is $C_{1-4}$alkylene; $R_{11}$ is selected from $C_{1-6}$alkyl, heteroaryl and aryl, each optionally substituted with 1 to 3 radicals independently selected from halo, cyano, hydroxyl, nitro, amino, $C_{1-4}$alkyl, halo-substituted-$C_{1-4}$alkyl, $C_{1-4}$alkoxy and halo-substituted-$C_{1-4}$alkoxy; $R_{12}$ and $R_{13}$ are independently selected from H and $C_{1-6}$alkyl; or $R_3$ and $R_4$ or $R_5$ and $R_6$ are each independently $C_{1-4}$alkyl and taken together with the carbon atoms to which they are attached can form a phenyl ring (such that the combined fused bicyclic group is quinolinyl); wherein said phenyl of the combination of $R_3$ and $R_4$ or $R_5$ and $R_6$ is optionally substituted with 1 to 3 radicals independently selected from cyano, amino, hydroxyl, nitro, halo, halo-substituted-$C_{1-4}$alkyl, $C_{1-4}$alkoxy and halo-substituted-$C_{1-4}$alkoxy;

or the pharmaceutically acceptable salts thereof.

In certain embodiments of such aforementioned compounds are compounds having a structure of Formula (Ia):

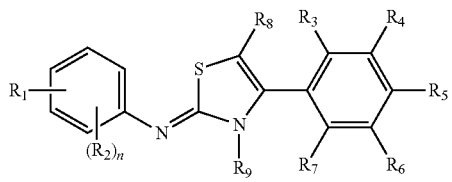

Formula (Ia)

wherein:

n is selected from 0, 1, 2, 3 and 4;

$R_8$ is selected from H, $C_{1-4}$-alkyl and phenyl optionally substituted with 1 to 3 radicals independently selected from halo, $C_{1-4}$alkyl, halo-substituted-$C_{1-4}$alkyl, $C_{1-4}$alkoxy and halo-substituted-$C_{1-4}$alkoxy;

$R_9$ is selected from $C_{1-6}$alkyl, halo-substituted-$C_{1-4}$alkyl and —$X_1R_{10}$; wherein $X_1$ is a bond or $C_{1-4}$alkylene; $R_{10}$ is $C_{3-8}$cycloalkyl;

$R_1$ is selected from —COOH, —$SO_3H$ and tetrazolyl;

each $R_2$ is independently selected from halo, $C_{1-4}$alkyl, halo-substituted-$C_{1-4}$alkyl, $C_{1-4}$alkoxy and halo-substituted-$C_{1-4}$alkoxy;

$R_3$, $R_4$, $R_5$, $R_6$ or $R_7$ are independently selected from H, cyano, hydroxyl, nitro, halo, $C_{1-4}$alkyl, halo-substituted-$C_{1-4}$alkyl, $C_{1-4}$alkoxy, halo-substituted-$C_{1-4}$alkoxy, $X_2OR_{11}$, —$X_2NR_{12}R_{13}$, —$X_2R_{11}$, —$X_2OX_3R_{11}$ and —$X_2OX_3OR_{11}$; wherein $X_2$ is selected from a bond and $C_{1-4}$alkylene; $X_3$ is $C_{1-4}$alkylene; $R_{11}$ is selected from $C_{1-6}$alkyl, heteroaryl and aryl, each optionally substituted with 1 to 3 radicals independently selected from halo, cyano, hydroxyl, nitro, amino, $C_{1-4}$alkyl, halo-substituted-$C_{1-4}$alkyl, $C_{1-4}$alkoxy and halo-substituted-$C_{1-4}$alkoxy; $R_{12}$ and $R_{13}$ are independently selected from H and $C_{1-6}$alkyl; or $R_3$ and $R_4$ or $R_5$ and $R_6$ are each independently $C_{1-4}$alkyl and taken together with the carbon atoms to which they are attached can form a phenyl ring; wherein said phenyl of the combination of $R_3$ and $R_4$ or $R_5$ and $R_6$ is optionally substituted with 1 to 3 radicals independently selected from cyano, amino, hydroxyl, nitro, halo, $C_{1-4}$alkyl, halo-substituted-$C_{1-4}$alkyl, $C_{1-4}$alkoxy and halo-substituted-$C_{1-4}$alkoxy;

or the pharmaceutically acceptable salts thereof.

In certain embodiments of such aforementioned compounds are compounds wherein $R_8$ is H or $C_{1-4}$alkyl.

In certain embodiments of such aforementioned compounds each $R_2$ is independently a halo, while in other embodiments of such aforementioned compounds each $R_2$ is independently selected from fluoro and bromo.

In certain embodiments of such aforementioned compounds are compounds having a structure of Formula (Ib):

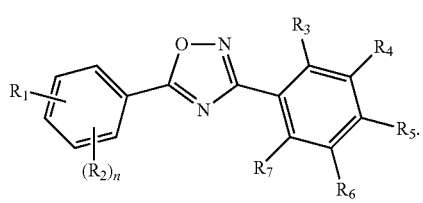

Formula (Ib)

In certain embodiments of such aforementioned compounds are compounds having a structure of Formula (Ic) or Formula (Id):

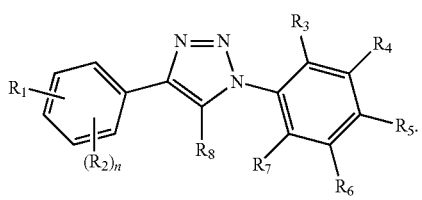

Formula (Ic)

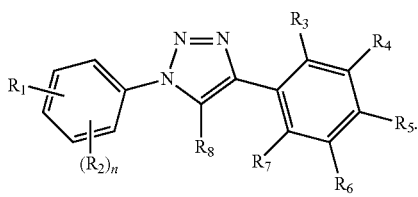

Formula (Id)

In certain embodiments of such aforementioned compounds are compounds selected from:

(Z)-4-(4-(3-cyanophenyl)-3-ethylthiazol-2(3H)-ylidene-amino)benzenesulfonic acid, (Z)-4-(4-(3,5-bis(trifluoromethylphenyl)-3-ethylthiazol-2(3H)-ylideneamino)benzenesulfonic acid, (Z)-4-(3-ethyl-5-methyl-4-phenylthiazol-2(3H)-ylidene-amino)benzenesulfonic acid, (Z)-4-(3-ethyl-4-(3-fluorophenyl)thiazol-2(3H)-ylidene-amino)benzenesulfonic acid, (Z)-4-(4-(3-bromophenyl)-3-ethylthiazol-2(3H)-ylidene-amino)benzenesulfonic acid, (Z)-4-(3-ethyl-4-(2-(trifluoromethoxy)phenyl)thiazol-2(3H)-ylideneamino)benzenesulfonic acid, (Z)-4-(4-(2,5-dichlorophenyl)-3-ethylthiazol-2(3H)-ylideneamino)benzenesulfonic acid, (Z)-4-(3-ethyl-4-(2-phenoxyphenyl)thiazol-2(3H)-ylidene-amino)benzoic acid, (Z)-N-(3-ethyl-4-phenylthiazol-2(3H)-ylidene)-4-(2H-tetrazol-5-yl)aniline, (Z)-4-(3-ethyl-4-phenylthiazol-2(3H)-ylideneamino)-2,3-difluorobenzoic acid, (Z)-4-(3-ethyl-4-(2-(trifluoromethyl)phenyl)thiazol-2(3H)-ylideneamino)benzoic acid, (Z)-4-(3-ethyl-4-(2-(trifluoromethoxy)phenyl)thiazol-2(3H)-ylideneamino)benzoic acid, (Z)-4-(3-ethyl-4-(3-(trifluoromethoxy)phenyl)thiazol-2(3H)-ylideneamino)benzoic acid, (Z)-4-(3-ethyl-4-phenylthiazol-2(3H)-ylideneamino)-2-fluorobenzoic acid, (Z)-2-bromo-4-(3-ethyl-4-phenylthiazol-2(3H)-ylidene-amino)benzoic acid, (Z)-4-(4-phenyl-3-propylthiazol-2(3H)-ylideneamino)benzoic acid, (Z)-4-(3-isopropyl-4-phenylthiazol-2(3H)-ylideneamino)benzoic acid, (Z)-4-(3-ethyl-4-(3-hydroxyphenyl)thiazol-2(3H)-ylidene-amino)benzoic acid, (Z)-4-(4-(2-bromo-5-hydroxyphenyl)-3-ethylthiazol-2(3H)-ylideneamino)benzoic acid, (Z)-4-(3-ethyl-4-(3-(2-methoxyethoxy)phenyl)thiazol-2(3H)-ylideneamino)benzoic acid, (Z)-4-(3-(cyclopropylmethyl)-4-phenylthiazol-2(3H)-ylideneamino)benzoic acid, (Z)-4-(3-sec-butyl-4-phenylthiazol-2(3H)-ylideneamino)
benzoic acid,
(Z)-4-(3-(2,2-difluoroethyl)-4-phenylthiazol-2(3H)-ylidene-
amino)benzoic acid,
(Z)-4-(4-phenyl-3-(2,2,2-trifluoroethyl)thiazol-2(3H)-ylide-
neamino)benzoic acid,
(Z)-4-(3-ethyl-4-phenylthiazol-2(3H)-ylideneamino)-2,3,5,
6-tetrafluorobenzoic acid,
(Z)-4-(4-(3-(benzyloxy)phenyl)-3-ethylthiazol-2(3H)-ylide-
neamino)benzoic acid,
(Z)-4-(3-ethyl-4-(3-(pyridin-2-ylmethoxy)phenyl)thiazol-2
(3H)-ylideneamino)benzoic acid,
(Z)-4-(3-ethyl-4-(2-methoxyphenyl)thiazol-2(3H)-ylidene-
amino)benzenesulfonic acid,
(Z)-4-(3-ethyl-4-(3-methoxyphenyl)thiazol-2(3H)-ylidene-
amino)benzenesulfonic acid,
(Z)-4-(4-(2-chlorophenyl)-3-ethylthiazol-2(3H)-ylidene-
amino)benzenesulfonic acid,
(Z)-4-(4-(3-chlorophenyl)-3-ethylthiazol-2(3H)-ylidene-
amino)benzenesulfonic acid
(Z)-4-(3-ethyl-4-(2-methoxyphenyl)thiazol-2(3H)-ylidene-
amino)benzoic acid,
(Z)-4-(3-ethyl-4-(3-methoxyphenyl)thiazol-2(3H)-ylidene-
amino)benzoic acid,
(Z)-4-(4-(2-chlorophenyl)-3-ethylthiazol-2(3H)-ylidene-
amino)benzoic acid,
(Z)-4-(4-(3-chlorophenyl)-3-ethylthiazol-2(3H)-ylidene-
amino)benzoic acid,
(Z)-4-(3-ethyl-4-phenylthiazol-2(3H)-ylideneamino)ben-
zoic acid,
(Z)-4-(3-ethyl-4-phenylthiazol-2(3H)-ylideneamino)benze-
nesulfonic acid,
(Z)-4-(4-(2,6-dichlorophenyl)-3-ethylthiazol-2(3H)-ylide-
neamino)benzoic acid,
(Z)-4-(4-(2,3-dichlorophenyl)-3-ethylthiazol-2(3H)-ylide-
neamino)benzoic acid,
(Z)-4-(3-ethyl-4-(naphthalen-1-yl)thiazol-2(3H)-ylidene-
amino)benzoic acid,
(Z)-4-(3-ethyl-4-(naphthalen-2-yl)thiazol-2(3H)-ylidene-
amino)benzoic acid,
(Z)-4-(4-(2-bromophenyl)-3-ethylthiazol-2(3H)-ylidene-
amino)benzoic acid,
(Z)-4-(4-(2-aminophenyl)-3-ethylthiazol-2(3H)-ylidene-
amino)benzoic acid,
(Z)-4-(3-ethyl-4-(2-nitrophenyl)thiazol-2(3H)-ylidene-
amino)benzoic acid,
(Z)-4-(3-ethyl-4-(2-(methylamino)phenyl)thiazol-2(3H)-
ylideneamino)benzoic acid,
(Z)-4-(4-(2-(dimethylamino)phenyl)-3-ethylthiazol-2(3H)-
ylideneamino)benzoic acid,
(Z)-4-(4-(3-bromophenyl)-3-ethylthiazol-2(3H)-ylidene-
amino)benzoic acid,
(Z)-4-(3-ethyl-4-(2-hydroxyphenyl)thiazol-2(3H)-ylidene-
amino)benzoic acid,
(Z)-4-(4-(3-cyanophenyl)-3-ethylthiazol-2(3H)-ylidene-
amino)benzoic acid,
(Z)-4-(4-(5-bromo-2-hydroxyphenyl)-3-ethylthiazol-2(3H)-
ylideneamino)benzoic acid,
3-[3-(4-Methoxyphenyl)-1,2,4-oxadiazol-5-yl]benzoic acid,
4-(3-(4-methoxyphenyl)-1,2,4-oxadiazol-5-yl)benzoic acid,
3-(3-(3-methoxyphenyl)-1,2,4-oxadiazol-5-yl)benzoic acid,
3-(1-(4-methoxyphenyl)-1H-1,2,3-triazol-4-yl)benzoic acid,
3-(4-(4-methoxyphenyl)-1H-1,2,3-triazol-1-yl)benzoic acid,
3-(5-(4-methoxyphenyl)-1,2,4-oxadiazol-3-yl)-benzoic
acid,
3-(4-p-tolyl-1H-1,2,3-triazol-1-yl)benzoic acid,
3-(4-(4-(trifluoromethyl)phenyl)-1H-1,2,3-triazol-1-yl)ben-
zoic acid,
3-(4-(4-chlorophenyl)-1H-1,2,3-triazol-1-yl)benzoic acid,
3-(4-(2-fluorophenyl)-1H-1,2,3-triazol-1-yl)benzoic acid,
3-(4-(4-ethylphenyl)-1H-1,2,3-triazol-1-yl)benzoic acid,
3-(4-(2,4-difluorophenyl)-1H-1,2,3-triazol-1-yl)benzoic
acid,
3-(4-(4-bromophenyl)-1H-1,2,3-triazol-1-yl)benzoic acid,
3-(1-(4-isopropylphenyl)-1H-1,2,3-triazol-4-yl)benzoic
acid,
3-(4-(4-ethylphenyl)-1H-1,2,3-triazol-1-yl)-5-methoxyben-
zoic acid,
3-(4-(4-ethylphenyl)-1H-1,2,3-triazol-1-yl)-5-fluorobenzoic
acid,
3-(1-(2-fluoro-4-methylphenyl)-1H-1,2,3-triazol-4-yl)ben-
zoic acid,
5-(4-(4-ethylphenyl)-1H-1,2,3-triazol-1-yl)-2-fluorobenzoic
acid and
3-(4-(4-ethylphenyl)-1H-1,2,3-triazol-1-yl)-4-fluorobenzoic
acid.

Another aspect provided herein are pharmaceutical compositions comprising a therapeutically effective amount of any aforementioned compound and a pharmaceutically acceptable carrier.

In certain embodiments, such pharmaceutical compositions are formulated for intravenous administration, intramuscular administration, oral administration, rectal administration, inhalation, nasal administration, topical administration, ophthalmic administration or otic administration.

In certain embodiments, such aforementioned pharmaceutical compositions are in a form selected from a tablet, a pill, a capsule, a liquid, an inhalant, a nasal spray solution, a suppository, a solution, an emulsion, an ointment, an eye drop and an ear drop.

In certain embodiments, such aforementioned pharmaceutical compositions further comprise one or more additional therapeutic agents.

Another aspect provided herein is medicaments for treating a disease or disorder where modulation of GPR120 is implicated, wherein the medicament comprises a therapeutically effective amount of any aforementioned compound. In certain embodiments of such medicaments, the disease or disorder is selected from diabetes, obesity, diabetes mellitus, dyslipidemia, hyperlipidemia, anorexia, hyperphagia, endocrine abnormalities, triglyceride storage disease, Bardet-Biedl syndrome, Lawrence-Moon syndrome, Prader-Labhart-Willi syndrome and cachexia.

Another aspect provided herein is the use of any aforementioned compound in the manufacture of a medicament for treating a disease or disorder in a patient where modulation of GPR120 is implicated.

Another aspect provided herein is methods for modulating GPR120 in a system or subject, wherein the method comprises administering to the system or the subject a therapeutically effective amount of any aforementioned compound, or pharmaceutically acceptable salt or pharmaceutical composition thereof, wherein the compound modulates GPR120 in the system or the subject. In certain embodiments of such methods, the system or subject is a cell or tissue system or a human or an animal subject. In certain embodiments of such methods, the compound is an agonist of GPR120.

Another aspect provided herein is methods for treating a disease or disorder where modulation of GPR120 is implicated, comprising administering to a system or subject in need of such treatment an effective amount of any aforementioned compound, or pharmaceutically acceptable salt or pharmaceutical composition thereof, thereby treating the disease or disorder. In certain embodiments of such methods, the system or subject is a cell or tissue system or a human or an animal subject. In certain embodiments of such methods, the compound is an agonist of GPR120. In certain embodiments of such methods, the disease or disorder is selected from diabetes, obesity, diabetes mellitus, dyslipidemia, hyperlipidemia, anorexia, hyperphagia, endocrine abnormalities, triglyceride storage disease, Bardet-Biedl syndrome, Lawrence-Moon syndrome, Prader-Labhart-Willi syndrome and cachexia. In certain embodiments of such methods, the disease or disorder is an autoimmune disease. In certain embodiments of such methods, the autoimmune disease is rheumatoid arthritis, systemic lupus erythematosus, idiopathic thrombocytopenic purpura, hemolytic anemia, or psoriasis.

Another aspect provided herein are compounds for use in a method of medical treatment, wherein the method of medical treatment is for treating a disease or disorder where modulation of GPR120 is implicated, wherein the disease or disorder is selected from diabetes, obesity, diabetes mellitus, dyslipidemia, hyperlipidemia, anorexia, hyperphagia, endocrine abnormalities, triglyceride storage disease, Bardet-Biedl syndrome, Lawrence-Moon syndrome, Prader-Labhart-Willi syndrome, cachexia, rheumatoid arthritis, systemic lupus erythematosus, idiopathic thrombocytopenic purpura, hemolytic anemia and psoriasis, and wherein the compound is a compound of Formula (I) provided herein.

DETAILED DESCRIPTION OF THE INVENTION

Definitions

The term "alkenyl" or "alkene," as used herein, refers to a partially unsaturated branched or straight chain hydrocarbon having at least one carbon-carbon double bond. Atoms oriented about the double bond are in either the cis (Z) or trans (E) conformation. In certain embodiments an alkenyl or alkene group is optionally substituted. As used herein, the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. Non-limiting examples of alkenyl groups, as used herein, include ethenyl, propenyl, butenyl, pentenyl, hexenyl, heptenyl, octenyl, nonenyl, decenyl and the like. As used herein, the terms "$C_2$-$C_3$alkene", "$C_2$-$C_4$alkene", "$C_2$-$C_5$alkene", "$C_2$-$C_6$alkene", "$C_2$-$C_7$alkene", and "$C_2$-$C_8$alkene" refer to an alkene group containing at least 2, and at most 3, 4, 5, 6, 7 or 8 carbon atoms, respectively. Non-limiting examples of alkene groups, as used herein, include ethene, propene, butene, pentene, hexene, heptene, octene, nonenel, decene and the like.

The term "alkenylene," as used herein, refers to a partially unsaturated branched or straight chain divalent hydrocarbon radical derived from an alkenyl group. In certain embodiments an alkenylene group is optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. In certain embodiments an alkyl group is optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. In certain embodiments an alkylene group is optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl" or "alkyne," as used herein, refers to a partially unsaturated branched or straight chain hydrocarbon having at least one carbon-carbon triple bond. In certain embodiments an alkynyl group or alkyne group is optionally substituted. As used herein, the terms "$C_2$-$C_3$alkynyl", "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 3, 4, 5, 6, 7 or 8 carbon atoms, respectively. Non-limiting examples of alkynyl groups, as used herein, include ethynyl, propynyl, butynyl, pentynyl, hexynyl, heptynyl, octynyl, nonynyl, decynyl and the like. As used herein, the terms "$C_2$-$C_3$alkyne", "$C_2$-$C_4$alkyne", "$C_2$-$C_5$alkyne", "$C_2$-$C_6$alkyne", "$C_2$-$C_7$alkyne", and "$C_2$-$C_8$alkyne" refer to an alkyne group containing at least 2, and at most 3, 4, 5, 6, 7 or 8 carbon atoms, respectively. Non-limiting examples of alkyne groups, as used herein, include ethyne, propyne, butyne, pentyne, hexyne, heptyne, octyne, nonyne, decyne and the like.

The term "alkynylene," as used herein, refers to a partially unsaturated branched or straight chain divalent hydrocarbon radical derived from an alkynyl group. In certain embodiments an alkynylene group is optionally substituted. As used herein, the terms "$C_2$-$C_3$alkynylene", "$C_2$-$C_4$alkynylene", "$C_2$-$C_5$alkynylene", "$C_2$-$C_6$alkynylene", "$C_2$-$C_7$alkynylene", and "$C_2$-$C_8$alkynylene" refer to an alkynylene group containing at least 2, and at most 3, 4, 5, 6, 7 or 8 carbon atoms respectively. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —$OR_a$, where $R_a$ is an alkyl group as defined herein. In certain embodiments an alkoxy group is optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. In certain embodiments an aryl group is optionally substituted with one or more substituents. Non-limiting examples of aryl groups, as used herein, include phenyl, naphthyl, fluorenyl, indenyl, azulenyl, anthracenyl and the like.

The term "arylene," as used herein refers to a divalent radical derived from an aryl group. In certain embodiments an arylene group is optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. In certain embodiments a cycloalkyl group is optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. In certain embodiments a haloalkyl group is optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. In certain embodiments a haloalkenyl group is optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. In certain embodiments a haloalkynyl group is optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. In certain embodiments a haloalkoxy group is optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. In certain embodiments a heteroaryl group is optionally substituted with one or more substituents. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, $C_1$-$C_4$alkyl or a nitrogen protecting group, with the proviso that the ring of said group does not contain two adjacent O or S atoms. In certain embodiments a heterocycloalkyl group is optionally substituted. Non-limiting examples of heterocycloalkyl groups, as used herein, include morpholino, pyrrolidinyl, pyrrolidinyl-2-one, piperazinyl, piperidinyl, piperidinyl-2-one, piperidinyl-3-one, piperidinyl-4-one, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "isocyanato," as used herein, refers to a —N=C=O group.

The term "isothiocyanato," as used herein, refers to a —N=C=S group.

The term "mercaptyl," as used herein, refers to an (alkyl)S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, =O, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$, —NRS(O)$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substitutent groups is done in accordance with the well-understood valence limitations of each group, for example =O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of Formula (I), a pharmaceutically acceptable salt, a pharmaceutically acceptable solvate, or prodrug thereof to a subject in need of treatment.

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent" as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "immunologically effective amount," as used herein, means that the administration of a sufficient amount to an individual, either in a single dose or as part of a series, that is effective for treatment or prevention of an immunological disease or disorder. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The term "inflammatory disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract; skin (dermatitis); or multiple organs and tissues (systemic lupus erythematosus).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an inhibitor or an enhancer.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound of Formula (I) described herein with other chemical components, such as carriers, stabilizers, diluents, dispersing agents, suspending agents, thickening agents, and/or excipients.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The compound names provided herein were obtained using ChemDraw Ultra 10.0 (CambridgeSoft®) or JChem version 5.0.3 (ChemAxon).

Other objects, features and advantages of the methods, compositions and combinations described herein will become apparent from the following detailed description. It should be understood, however, that the detailed description and the specific examples, while indicating specific embodiments, are given by way of illustration only.

Compounds

Provided herein are compounds, pharmaceutically acceptable salts, solvates, N-oxides, prodrugs and isomers thereof that are modulators of G protein-coupled receptors (GPCR's). In certain embodiments such compounds, pharmaceutically acceptable salts, solvates, N-oxides, prodrugs and isomers thereof are agonists of G protein-coupled receptors. In certain embodiments such compounds, pharmaceutically acceptable salts, solvates, N-oxides, prodrugs and isomers thereof are modulators of G protein coupled receptor 120 (GPR120). In certain embodiments such compounds, pharmaceutically acceptable salts, solvates, N-oxides, prodrugs and isomers thereof are agonists of G protein coupled receptor 120 (GPR120).

Further provided herein are compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, for the treatment and/or prevention of diseases and/or disorders associated with G protein coupled receptors. In certain embodiments such compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, are for the treatment and/or prevention of diseases and/or disorders associated with G protein coupled receptor 120 (GPR120). In certain embodiments, such diseases and/or disorders associated with G protein coupled receptor 120 (GPR120) include, but are not limited to, metabolic diseases and/or disorders and eating disorders. Such metabolic diseases and/or disorders and eating disorders include, but are not limited to, obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia. In certain embodiments such compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, control appetite and/or control weight gain.

Further provided herein are methods for the treatment and/or prevention of diseases and/or disorders associated with G protein coupled receptors. In certain embodiments such methods are for the treatment and/or prevention of diseases and/or disorders associated with G protein coupled receptor 120 (GPR120). In certain embodiments, such diseases and/or disorders associated with G protein coupled receptor 120 (GPR120) include, but are not limited to, metabolic diseases and/or disorders and eating disorders. Such metabolic diseases and/or disorders and eating disorders include, but are not limited to, obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia. In certain embodiments such methods are used to control appetite. In certain embodiments such methods are used to control weight gain. In certain embodiments such methods are used to control weight loss.

The aforementioned compounds and pharmaceutically acceptable salts, solvates, N-oxides, prodrugs and isomers thereof, are compounds having structures according to Formula (I), wherein Formula (I) is

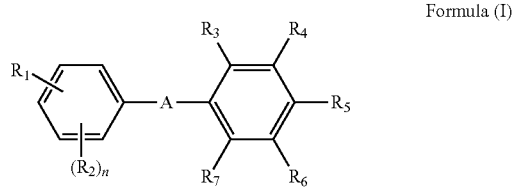

Formula (I)

wherein:
n is selected from 0, 1, 2, 3 and 4;
A is selected from:

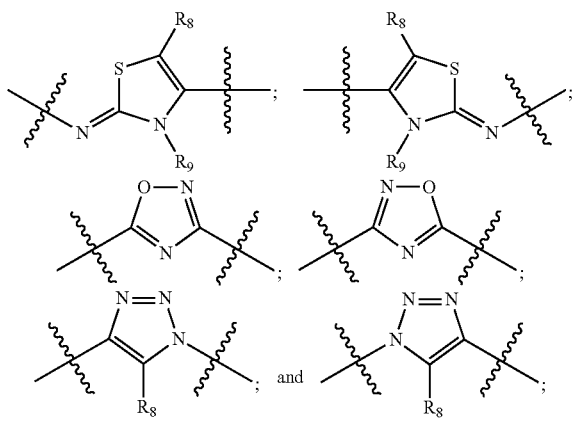

wherein:
R$_8$ is selected from H, C$_{1-4}$alkyl and phenyl optionally substituted with 1 to 3 radicals independently selected from halo, C$_{1-4}$alkyl, halo-substituted-C$_{1-4}$alkyl, C$_{1-4}$alkoxy and halo-substituted-C$_{1-4}$alkoxy;
R$_9$ is selected from C$_{1-6}$alkyl, halo-substituted-C$_{1-4}$alkyl and —X$_1$R$_{10}$; wherein X$_1$ is a bond or C$_{1-4}$alkylene; R$_{10}$ is C$_{3-8}$cycloalkyl;
R$_1$ is selected from —COOH, —SO$_3$H and tetrazolyl;

R$_2$ is selected from halo, C$_{1-4}$alkyl, halo-substituted-C$_{1-4}$alkyl, C$_{1-4}$alkoxy and halo-substituted-C$_{1-4}$alkoxy;
R$_3$, R$_4$, R$_5$, R$_6$ or R$_7$ are independently selected from H, cyano, hydroxyl, nitro, halo, C$_{1-4}$alkyl, halo-substituted-C$_{1-4}$alkyl, C$_{1-4}$alkoxy, halo-substituted-C$_{1-4}$alkoxy, X$_2$OR$_{11}$, —X$_2$NR$_{12}$R$_{13}$, —X$_2$R$_{11}$ and —X$_2$OX$_3$OR$_{11}$; wherein X$_2$ is selected from a bond and C$_{1-4}$alkylene; X$_3$ is C$_{1-4}$alkylene; R$_{11}$ is selected from C$_{1-6}$alkyl and aryl optionally substituted with 1 to 3 radicals independently selected from halo, cyano, hydroxyl, nitro, amino, C$_{1-4}$alkyl, halo-substituted-C$_{1-4}$alkyl, C$_{1-4}$alkoxy and halo-substituted-C$_{1-4}$alkoxy; R$_{12}$ and R$_{13}$ are independently selected from H and C$_{1-6}$alkyl; or
R$_3$ and R$_4$ or R$_5$ and R$_6$ together with the carbon atoms to which they are attached can form a phenyl ring (such that the combined fused bicyclic group is quinolinyl); wherein said phenyl of the combination of R$_3$ and R$_4$ or R$_5$ and R$_6$ is optionally substituted with 1 to 3 radicals independently selected from cyano, amino, hydroxyl, nitro, halo, C$_{1-4}$alkyl, halo-substituted-C$_{1-4}$alkyl, C$_{1-4}$alkoxy and halo-substituted-C$_{1-4}$alkoxy;
or the pharmaceutically acceptable salts thereof.

In certain embodiments of such aforementioned compounds are compounds having a structure of Formula (Ia):

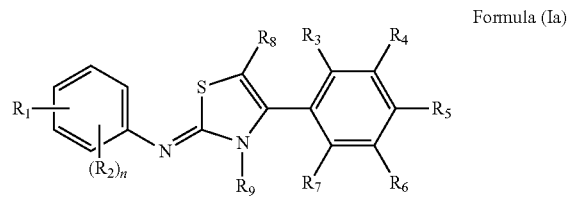

Formula (Ia)

wherein:
n is selected from 0, 1, 2, 3 and 4;
R$_8$ is selected from H, C$_{1-4}$alkyl and phenyl optionally substituted with 1 to 3 radicals independently selected from halo, C$_{1-4}$alkyl, halo-substituted-C$_{1-4}$alkyl, C$_{1-4}$alkoxy and halo-substituted-C$_{1-4}$alkoxy;
R$_9$ is selected from C$_{1-6}$alkyl, halo-substituted-C$_{1-4}$alkyl and —X$_1$R$_{10}$; wherein X$_1$ is a bond or C$_{1-4}$alkylene; R$_{10}$ is C$_{3-8}$cycloalkyl;
R$_1$ is selected from —COOH, —SO$_3$H and tetrazolyl;
each R$_2$ is independently selected from halo, C$_{1-4}$alkyl, halo-substituted-C$_{1-4}$alkyl, C$_{1-4}$alkoxy and halo-substituted-C$_{1-4}$alkoxy;
R$_3$, R$_4$, R$_5$, R$_6$ or R$_7$ are independently selected from H, cyano, hydroxyl, nitro, halo, C$_{1-4}$alkyl, halo-substituted-C$_{1-4}$alkyl, C$_{1-4}$alkoxy, halo-substituted-C$_{1-4}$alkoxy, X$_2$OR$_{11}$, —X$_2$NR$_{12}$R$_{13}$, —X$_2$R$_{ii}$, —X$_2$OX$_3$R$_{11}$ and —X$_2$OX$_3$OR$_{11}$; wherein X$_2$ is selected from a bond and C$_{1-4}$alkylene; X$_3$ is C$_{1-4}$alkylene; R$_{11}$ is selected from C$_{1-6}$alkyl, heteroaryl and aryl, each optionally substituted with 1 to 3 radicals independently selected from halo, cyano, hydroxyl, nitro, amino, C$_{1-4}$alkyl, halo-substituted-C$_{1-4}$alkyl, C$_{1-4}$alkoxy and halo-substituted-C$_{1-4}$alkoxy; R$_{12}$ and R$_{13}$ are independently selected from H and C$_{1-6}$alkyl; or
R$_3$ and R$_4$ or R$_5$ and R$_6$ are each independently C$_{1-4}$alkyl and taken together with the carbon atoms to which they are attached can form a phenyl ring; wherein said phenyl of the combination of R$_3$ and R$_4$ or R$_5$ and R$_6$ is optionally substituted with 1 to 3 radicals independently selected from cyano, amino, hydroxyl, nitro, halo, $C_{1-4}$alkyl, halo-substituted-$C_{1-4}$alkyl, $C_{1-4}$alkoxy and halo-substituted-$C_{1-4}$alkoxy;

or the pharmaceutically acceptable salts thereof.

In certain embodiments of such aforementioned compounds are compounds wherein $R_8$ is H or $C_{1-4}$alkyl.

In certain embodiments of such aforementioned compounds each $R_2$ is independently a halo, while in other embodiments of such aforementioned compounds each $R_2$ is independently selected from fluoro and bromo.

In certain embodiments of such aforementioned compounds are compounds having a structure of Formula (Ib):

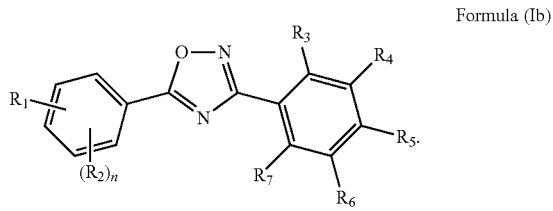

Formula (Ib)

In certain embodiments of such aforementioned compounds are compounds having a structure of Formula (Ic) or Formula (Id):

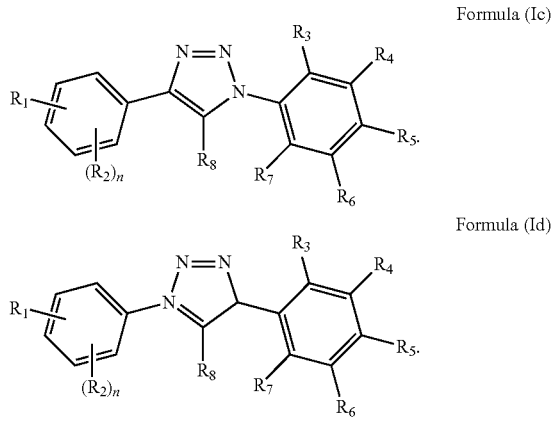

Formula (Ic)

Formula (Id)

The compounds of Formulas (I), (Ia), (Ib), (Ic) and (Id), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Processes for Making Compounds of Formula (I)

General procedures for preparing compounds of Formula (I) are described in the Examples, infra. In the reactions described, reactive functional groups, for example hydroxyl, amino, imino, thio or carboxy groups, where these are desired in the final product, may be protected to avoid their unwanted participation in the reactions. Conventional protecting groups may be used in accordance with standard practice (see such as, by way of example only, T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) described herein are prepared from the corresponding base addition salt or acid addition salt form, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, the compounds of Formula (I) described herein in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) described herein are prepared using methods known to those of ordinary skill in the art (such as, by way of example only, for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxy-alkylcarbanochloridate, paranitrophenyl carbonate, or the like).

In certain embodiments, the compounds of Formula (I) described herein are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, the compounds of Formula (I) described herein are prepared or formed, as solvates (such as, by way of example only, hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, the compounds of Formula (I) described herein are prepared as their individual stereoisomers. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (such as, by way of example only, crystalline diastereomeric salts). Diastereomers have distinct physical properties (such as, by way of example only, melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are made by processes described herein and as illustrated in the Examples. In certain embodiments, compounds of Formula (I) are made by (a) optionally converting a compound of the invention into a pharmaceutically acceptable salt;
(b) optionally converting a salt form of a compound of the invention to a non-salt form;
(c) optionally converting an unoxidized form of a compound of the invention into a pharmaceutically acceptable N-oxide;
(d) optionally converting an N-oxide form of a compound of the invention to its unoxidized form;
(e) optionally resolving an individual isomer of a compound of the invention from a mixture of isomers;
(f) optionally converting a non-derivatized compound of the invention into a pharmaceutically acceptable prodrug derivative; and
(g) optionally converting a prodrug derivative of a compound of the invention to its non-derivatized form.

Non-limiting examples of synthetic schemes used to make compounds of Formula (I) described herein are illustrated in reaction schemes (I)-(IV), wherein $R^1$, $R^2$, $R^3$, $R^4$, $R^5$, $R^6$, $R^7$, $R^7$, and $R^9$ are as defined herein.

Reaction scheme (I) illustrates the synthesis of substituted thiazoles having a structure of Formula (Ia).

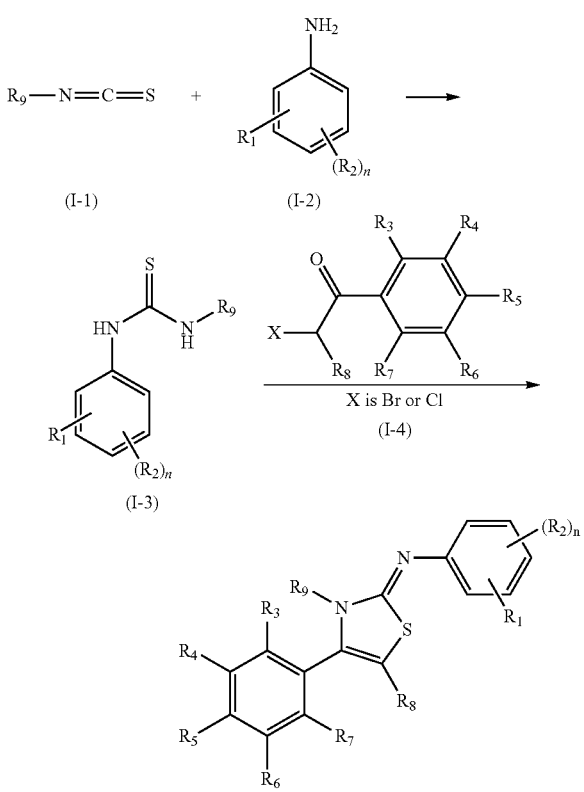

In Reaction Scheme (I) compounds of Formula (Ia) are prepared by first reacting isothiocyanate (I-1) with amine (I-2) in the presence of a suitable solvent and heat to give thiourea (I-3). Solvents used in such reactions include, but are not limited to acetonitrile (ACN). Thiourea (I-3) is then reacted with halo-derivative (I-4) in the presence of a suitable solvent and heat to give compounds of Formula (Ia). Solvents used in such reactions include, but are not limited to methanol. In certain embodiments, the synthetic methods provided by Kasmi, Souad; Hamelin, Jack; Benhaoua, Hadj, *Microwave-assisted solvent-free synthesis of iminothiazolines*, Tetrahedron Letters (1998), 39(44), 8093-8096; Korohoda, Maria Jolanta; Bojarska, Aleksandra Barbara, *Introduction of selenium to heterocyclic compounds. Part IV, Structure of 2-imino-4-thiazoline derivatives*, Polish Journal of Chemistry (1984), 58(4-5-6), 447-53; and Singh, Harjit; Ahuja, A. S.; Malhotra, N, *Reactions of N,N-dialkyl-N'-arylthioureas with α-halo ketones and of 2-substituted imino-1,3-oxathioles with heterocumulenes*, Indian Journal of Chemistry, Section B: Organic Chemistry Including Medicinal Chemistry (1980), 19B(12), 1019-22 have been modified for the synthesis of compounds provided herein.

Reaction scheme (II) illustrates the synthesis of substituted oxadizoles having a structure of Formula (Ib).

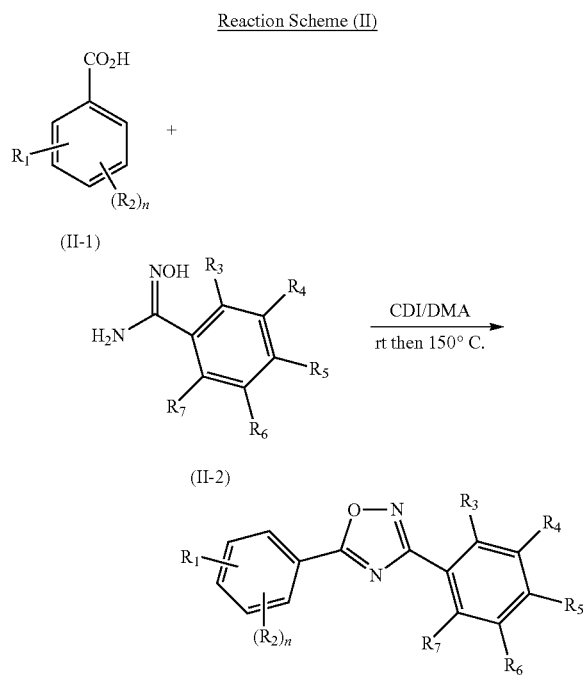

In Reaction Scheme (II) compounds of Formula (Ib) are prepared by reacting carboxylic acid (II-1) with hydroxylamine (II-2) in the presence of a suitable solvent and 1,1'-carbonyldiimidazole. Solvents used in such reactions include, but are not limited to N,N-dimethyl acetamide (DMA). In certain embodiments, the synthetic methods provided by Ooi, Ngan Sim; Wilson, David A., *Formation and thermal reaction of O-(N-acetylbenzimidoyl)benzamidoxime: comparison with the formation of 3,5-disubstituted 1,2,4-oxadiazoles from O-acetylarylamidoximes and O-aroylacetamidoximes*, Journal of the Chemical Society, Perkin Transactions 2: Physical Organic Chemistry (1972-1999), (1980), (12), 1792-9 and Lloyd, John; Schmidt, Joan B.; Rovnyak, George; Ahmad, Saleem; Atwal, Karnail S.; Bisaha, Sharon N.; Doweyko, Lidia M.; Stein, Philip D.; Traeger, Sarah C.; Mathur, Arvind; Conder, Mary Lee; DiMarco, John; Harper, Timothy W.; Jenkins-West, Tonya; Levesque, Paul C.; Normandin, Diane E.; Russell, Anita D.; Serafino, Randolph P.; Smith, Mark A.; Lodge, Nicholas J., *Design and synthesis of 4-substituted benzamides as potent, selective, and orally bioavailable IKs blockers*, Journal of Medicinal Chemistry (2001), 44(23), 3764-3767 have been modified for the synthesis of compounds provided herein.

Reaction scheme (III) illustrates the synthesis of substituted triazoles having a structure of Formula (Id).

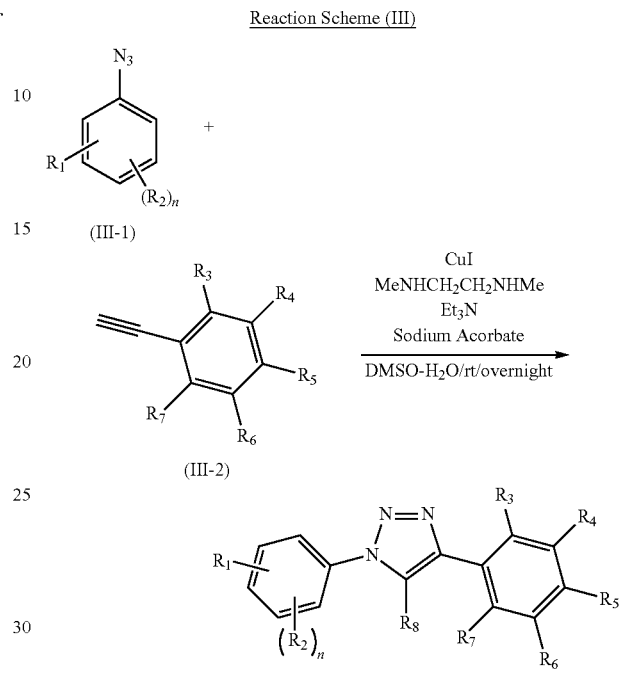

In Reaction Scheme (III) compounds of Formula (Id) are prepared using "click" chemistry wherein azide (III-1) is reacted with alkyne (III-2) in the presence of a suitable solvent, a copper catalyst and an oxidizing agent. Solvents used in such reactions include, but are not limited to dimethyl sulfoxide and water. In certain embodiments, the synthetic methods provided by Hirose T, Sunazuka T, Noguchi Y, et al., Rapid '*SAR' via click chemistry: an alkyne-bearing spiramycin is fused with diverse azides to yield new triazole-antibacterial candidates*, Heterocycles. 2006; 69:55-61; Rostovtsev V V, Green L G, Fokin V V, Sharpless K B., *A stepwise Huisgen cycloaddition process: copper(I)-catalyzed regioselective "ligation" of azides and terminal alkynes*, Angew. Chem., Int. Ed. 2002; 41(14):2596-2599, and Wang Q, Chan T R, Hilgraf R, Fokin V V, Sharpless K B, Finn M G., *Bioconjugation by copper(I)-catalyzed azide-alkyne [3+2]cycloaddition*, J. Am. Chem. Soc. 2003; 125(11):3192-3193, have been modified for the synthesis of compounds provided herein.

Reaction scheme (IV) illustrates the synthesis of substituted triazoles having a structure of Formula (Ic).

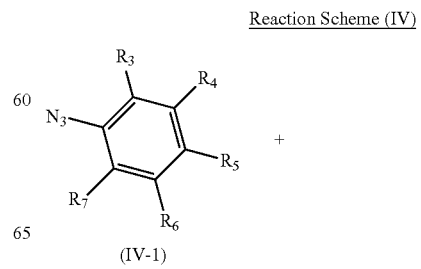

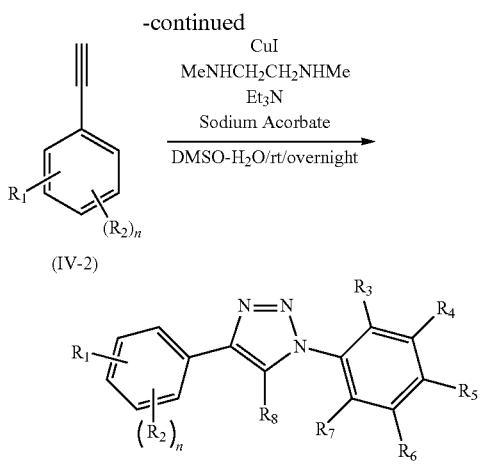

In Reaction Scheme (IV) compounds of Formula (Ic) are prepared using "click" chemistry wherein azide (IV-1) is reacted with alkyne (IV-2) in the presence of a suitable solvent, a copper catalyst and an oxidizing agent. Solvents used in such reactions include, but are not limited to dimethyl sulfoxide and water.

Detailed examples of the synthesis of compounds of Formula (I) can be found in the Examples, infra.

Pharmacology and Utility

G protein coupled receptor 120 (GPR120) is an orphan G protein-coupled receptor that is abundantly expressed in intestine, and functions as a receptor for unsaturated long-chain free fatty acids (FFAs). Stimulation of GPR120 by FFAs has been reported to promote the secretion of glucagon-like peptide-1 (GLP-1) and increase circulating insulin, and to activate the extracellular signal-regulated kinase (ERK) cascade. Peripherally, GLP-1 affects gut motility, and inhibits gastric acid and glucagon secretion. In the central nervous system, GLP-1 induces satiety, leading to reduced weight gain. In the pancreas, GLP-1 induces expansion of insulin-secreting β-cell mass, in addition to the augmentation of glucose-stimulated insulin secretion. See Hirasawa A, Tsumaya K, Awaji T, Katsuma S, Adachi T, Yamada M, Sugimoto Y, Miyazaki S, Tsujimoto G., *Free fatty acids regulate gut incretin glucagon-like peptide-1 secretion through GPR120*, Nat. Med. 2005 January; 11(1):90-4; Briscoe C P, Peat A J, McKeown S C, Corbett D F, Goetz A S, Littleton T R, McCoy D C, Kenakin T P, Andrews J L, Ammala C, Formwald J A, Ignar D M, Jenkinson S., *Pharmacological regulation of insulin secretion in MIN6 cells through the fatty acid receptor GPR40: identification of agonist and antagonist small molecules*, Br J. Pharmacol. 2006 July; 148(5):619-28; Katsuma S, Hatae N, Yano T, Ruike Y, Kimura M, Hirasawa A, Tsujimoto G., *Free fatty acids inhibit serum deprivation-induced apoptosis through GPR120 in a murine enteroendocrine cell line STC*-1, J. Biol. Chem. 2005 May 20; 280(20):19507-15; Gotoh C, Hong Y H, Iga T, Hishikawa D, Suzuki Y, Song S H, Choi K C, Adachi T, Hirasawa A, Tsujimoto G, Sasaki S, Roh S G., *The regulation of adipogenesis through GPR120*, Biochem Biophys Res Commun. 2007 Mar. 9; 354(2):591-7; Rayasam G V, Tulasi V K, Davis J A, Barisal V S., *Fatty acid receptors as new therapeutic targets for diabetes*, Expert Opin Ther Targets. 2007 May; 11(5):661-71; Tanaka T, Katsuma S, Adachi T, Koshimizu T A, Hirasawa A, Tsujimoto G., *Free fatty acids induce cholecystokinin secretion through GPR120*, Naunyn Schmiedebergs Arch Pharmacol. 2007 Oct. 31, and Matsumura S, Mizushige T, Yoneda T, Iwanaga T, Tsuzuki S, Inoue K, Fushiki T, *GPR expression in the rat taste bud relating to fatty acid sensing*, Biomed Res. 2007 February; 28(1):49-55.

Given the significance of GLP-1 as a potent insulinotropic incretin and in appetite and feeding control, GPR120 is a promising target for the treatment of diabetes, obesity and other eating disorders. Because of the importance of GPCRs as targets for drug action and development, there remains a need for the development of agents which modulate GPCR function.

The compounds provided herein are useful for modulating G protein-coupled receptors (GPCRs). In certain embodiments such compounds are useful for modulating G protein-coupled receptors 120 (GPR120). In certain embodiments such compounds are useful as GPR120 agonists.

Compounds provided herein are useful for treating conditions mediated by GPR120, including, but are not limited to, diabetes (such as, by way of example only, diabetes mellitus) and dyslipidemia (such as, by way of example only, hyperlipidemia, obesity and anorexia).

Compounds provided herein modulate G protein-coupled receptors, and as such, are useful for treating diseases or disorders in which GPCR's contribute to the pathology and/or symptomology of the disease or disorder. In certain embodiments, the compounds provided hereinare used to prevent, ameliorate or treat a condition mediated by G protein-coupled receptor 120 (GPR120). Conditions mediated by GPR120 include, but are not limited to, obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia.

Obesity is defined as a body mass index (BMI) of 30 kg/m$^2$ or more (National Institute of Health, Clinical Guidelines on the Identification, Evaluation, and Treatment of Overweight and Obesity in Adults (1998)). In certain embodiments, compounds provided herein are used to prevent, ameliorate or treat a condition characterized by a body mass index (BMI) of 25 kg/m$^2$ or more, 26 kg/m$^2$ or more, 27 kg/m$^2$ or more, 28 kg/m$^2$ or more, 29 kg/m$^2$ or more, 29.5 kg/m$^2$ or more, or 29.9 kg/m$^2$ or more, all of which are typically referred to as overweight (National Institute of Health, Clinical Guidelines on the Identification, Evaluation, and Treatment of Overweight and Obesity in Adults (1998)).

In other embodiments, compounds provided herein are useful as an agent for regulating glycerol production from adipocytes, an agent for regulating blood glycerol, an agent for regulating lipolysis, an insulin resistance regulating agent, a stress regulating agent, an agent for regulating adrenocorticotropic hormone (ACTH) secretion, an agent for regulating growth hormone secretion, and an agent for regulating glucagon-like peptide-1 (GLP-1) secretion.

In other embodiments, compounds provided herein that are GPR120 agonists, or that potentiate the binding affinity of free fatty acids to GPR120, are useful as an agent for suppressing glycerol production from adipocytes, an agent for lowering blood glycerol, an agent for suppressing lipolysis, an agent for suppressing insulin resistance, a stress regulating agent, an adrenocorticotropic hormone (ACTH) secretion suppressing agent, a growth hormone secretion suppressing agent and a glucagon-like peptide-1 (GLP-1) secretion promoting agent.

In certain embodiments, compounds provided herein that are GPR120 agonists are useful as an adrenocorticotropic hormone (ACTH) secretion suppressing agent and are useful for preventing/treating related diseases, such as ACTH-producing tumor, Cushing's disease, infectious disease, secondary adrenocortical insufficiency, peptic ulcer, diabetes mellitus, mental disorder, cataract, glaucoma, tuberculous disease, hypertension, Cushing's syndrome, central obesity, edema, hypertension, menstrual disorder, extensive stretch mark, hirsutism, full moon face, osteoporosis, hemorrhagic diathesis, depression, anxiety, muscular atrophy, loss of muscle strength, hypokalemia, hypercholesterolemia, impaired glucose resistance, leukocytosis, and adrenocortical atrophy.

In certain embodiments, compounds provided herein are GPR120 antagonists, or reduce the binding affinity of free fatty acids to GPR120, and are useful as an agent for promoting glycerol production from adipocytes, an agent for increasing blood glycerol, an agent for promoting lipolysis, an agent for promoting insulin resistance, a stress regulating agent, an agent for promoting adrenocorticotropic hormone (ACTH) secretion, an agent for promoting growth hormone secretion and an agent for suppressing glucagon-like peptide-1 (GLP-1) secretion. In certain embodiments, such GPR120 antagonists useful as an agent for promoting adrenocorticotropic hormone (ACTH) secretion are useful for preventing/treating connective tissue diseases, kidney diseases, respiratory diseases, alimentary diseases, neuromuscular diseases, blood diseases, endocrine-metabolic diseases, skin diseases and anaphylactic shock. Such connective tissue diseases include, but are not limited to, chronic articular rheumatism, systemic lupus erythematosus, polymyositis, rheumatic fever and scleroderma. Such kidney diseases include, but are not limited to, nephrosis. Such respiratory diseases include, but are not limited to, bronchial asthma, pulmonary tuberculous pleuritis, sarcoidosis and diffuse interstitial pneumonia. Such alimentary diseases include, but are not limited to, ulcerative colitis, cholestatic acute hepatitis, fulminant hepatitis, chronic hepatitis and cirrhosis). Such neuromuscular diseases include, but are not limited to, encephalomyelitis, peripheral neuritis, multiple sclerosis, myasthenia gravis and facial paralysis. Such blood diseases include, but are not limited to, hemolytic anemia, agranulocytosis, purpura, aplastic anemia, leukemia, and malignant lymphoma. Such endocrine-metabolic diseases include, but are not limited to, acute or chronic adrenocortical insufficiency, adrenogenital syndrome, malignant exophthalmos due to thyroid gland disease and ACTH isolated deficiency. Such skin diseases include, but are not limited to, urticaria, eczema, dermatitis, herpes zoster, psoriasis and drug allergy.

In other embodiments, compounds provided herein are useful as an agent for preventing/treating diabetes mellitus, impaired glucose tolerance, ketosis, acidosis, diabetic neuropathy, diabetic nephropathy, diabetic retinopathy, hyperlipemia, arteriosclerosis, angina pectoris, myocardial infarction, sexual dysfunction, obesity, pituitary dysfunctions (such as, by way of example only, hypopituitarism, pituitary dwarfism, diabetes insipidus, acromegaly, Cushing's disease, hyperprolactinemia, and syndrome of inappropriate secretion of anti-diuretic hormone), cancer (such as, by way of example only, colorectal cancer), deficits in memory and learning, pancreatic exhaustion, hypoglycemia, insulin allergy, lipotoxicity, fatty atrophy, cancerous cachexia, hyperinsulinemia, hyperglycemia, disorder caused by high FFA flux, hypertriglyceridemia, fatty liver, dysfunction of heat production, cholelithiasis, eating disorder, anorexia, secretion disorders of intestinal hormones (such as, by way of example only, cholecystokinin (CCK), gastric inhibitory peptide (GIP), gastrin, glucagon-like peptide-1 (GLP-1), somatostatin, gastrin-releasing peptide, secretin, vasoactive intestinal peptide, motilin, substance P, neurotensin, galanin, neuropeptide Y, enkephalins, and peptide YY) or circulatory diseases.

In certain embodiments, compounds provided herein are GPR120 agonists and are useful for preventing and/or treating diabetes mellitus, hyperlipemia, arteriosclerosis, angina pectoris or myocardial infarction, while in other embodiments compounds provided herein are GPR120 antagonists and are useful for preventing and/or treating anorexia and obesity, including obesity with visceral fat accumulation.

In other embodiments, compounds provided herein are useful as agents for preventing and/or treating diseases including, but not limited to, arteriosclerosis, arteriosclerotic diseases and their secondary diseases (such as, by way of example only, acute coronary syndrome, atherosclerosis, peripheral arterial disease, acute myocardial infarction, unstable angina, ischemic heart diseases, restenosis after percutaneous transluminal coronary angioplasty (PTCA), myocardial infarction, angina pectoris, arteriosclerosis including angiocalcinosis, intermittent claudication, apoplexy, cerebral infarction, cerebral embolism, brain hemorrhage, lacunar infarction, cerebrovascular dementia, gangrene, glomerulosclerosis, nephropathy and Tangier disease), vascular lesions in atherosclerosis and their secondary diseases (such as, by way of example only, coronary heart disease (CHD) and cerebral ischemia), and lipid dysbolism and its secondary diseases.

Such autoimmune mediated disorders include, but are not limited to, rheumatoid arthritis (RA), systematic lupus erythematosus (SLE), hemolytic anemia, lupus, primary binary cirrhosis (PBC) and idiopathic thrombocytopenic purpura (ITP).

Respiratory diseases include but are not limited to, asthma, rhinitis, COPD, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, acute and chronic rhinitis including rhinitis medicamentosa, and vasomotor rhinitis; perennial and seasonal allergic rhinitis including rhinitis nervosa (hay fever).

Dermatological diseases and/or disorders include, but are not limited to, dermatitis and eczema such as, by way of example only, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis and pityriasis alba.

Treatment of Diseases Associated with and/or Mediated by G Protein-Coupled Receptors Compounds of Formula (I), pharmaceutically acceptable salts, solvates, N-oxides, prodrugs and isomers thereof, pharmaceutical compositions, and combination therapies provided herein are modulators of G protein-coupled receptors, and are used in the treatment and/or prevention of diseases and/or disorders associated with or mediated by G protein-coupled receptors. Compounds of Formula (I), pharmaceutically acceptable salts, solvates, N-oxides, prodrugs and isomers thereof, pharmaceutical compositions, and combination therapies provided herein are modulators of G protein-coupled receptor 120, and are used in the treatment and/or prevention of diseases and/or disorders associated with or mediated by G protein-coupled receptor 120. Such diseases and/or disorders include, but are not limited to, those provided herein.

In certain embodiments, compounds of Formula (I), pharmaceutically acceptable salts, solvates, N-oxides, prodrugs and isomers thereof, pharmaceutical compositions, and combination therapies provided herein are agonists of G protein-coupled receptors, and are used in the treatment and/or prevention of diseases and/or disorders associated with or mediated by G protein-coupled receptors. In certain embodiments, compounds of Formula (I), pharmaceutically acceptable salts, solvates, N-oxides, prodrugs and isomers thereof, pharmaceutical compositions, and combination therapies provided herein are agonists of G protein-coupled receptor 120, and are used in the treatment and/or prevention of diseases and/or disorders associated with or mediated by G protein-coupled receptor 120. Such diseases and/or disorders include, but are not limited to, those provided herein.

In certain embodiments, compounds of Formula (I), pharmaceutically acceptable salts, solvates, N-oxides, prodrugs and isomers thereof, pharmaceutical compositions, and combination therapies provided herein are antagonists of G protein-coupled receptors, and are used in the treatment and/or prevention of diseases and/or disorders associated with or mediated by G protein-coupled receptors. In certain embodiments, compounds of Formula (I), pharmaceutically acceptable salts, solvates, N-oxides, prodrugs and isomers thereof, pharmaceutical compositions, and combination therapies provided herein are antagonists of G protein-coupled receptor 120, and are used in the treatment and/or prevention of diseases and/or disorders associated with or mediated by G protein-coupled receptor 120. Such diseases and/or disorders include, but are not limited to, those provided herein.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, acute and chronic rhinitis including rhinitis medicamentosa, and vasomotor rhinitis; perennial and seasonal allergic rhinitis including rhinitis nervosa (hay fever).

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of dermatological disorders including, but not limited to, psoriasis, dermatitis, eczema, atopic dermatitis, contact dermatitis, urushiol-induced contact dermatitis, eczematous dermatoses, and delayed-type hypersensitivity reactions; phyto- and photodermatitis; seborrhoeic dermatitis, dermatitis herpetiformis, lichen simplex chronicus, lichen planus, lichen sclerosus et atrophica, discoid lupus erythematosus, diaper rash, erythroderma, prurigo nodularis, itch, pruritus ani, nummular dermatitis, dyshidrosis and pityriasis alba.

In certain embodiments, the compounds of Formula (I), pharmaceutically acceptable salts, solvates, N-oxides, prodrugs and isomers thereof, and pharmaceutical compositions and combination therapies provided herein are used as immunosuppressant agents to treat and/or prevent rheumatoid arthritis (RA), multiple sclerosis (MS), systemic lupus erythematosus (SLE), immune thrombocytopenic purpura (ITP), hemolytic anemia and transplant rejection.

Compounds of Formula (I), pharmaceutically acceptable salts, solvates, N-oxides, prodrugs and isomers thereof, pharmaceutical compositions, and combination therapies provided herein are used in methods for modulating G protein-coupled receptors in a subject (human or other mammal) for the treatment and/or prevention of diseases and/or disorders associated with or mediated by G protein-coupled receptors. In certain embodiments, compounds of Formula (I), pharmaceutically acceptable salts, solvates, N-oxides, prodrugs and isomers thereof, pharmaceutical compositions, and combination therapies provided herein are used in methods for modulating G protein-coupled receptor 120 in a subject (human or other mammal) for the treatment and/or prevention of diseases and/or disorders associated with or mediated by G protein-coupled receptor 120. In certain embodiments, such methods include administering to a subject a compound of Formula (I), or a pharmaceutical composition containing a compound of Formula (I), in an effective amount thereby modulating G protein-coupled receptors, including G protein-coupled receptor 120, in a subject.

In certain embodiments, the methods for the treatment of a subject suffering from a disease and/or disorder associated with or mediated by G protein-coupled receptors, including G protein-coupled receptor 120, include administering to the subject an effective amount of a compound of Formula (I), or a pharmaceutically acceptable salt, solvate thereof, either alone or as part of a pharmaceutical composition as described herein.

In certain embodiments, are methods for treating a disease or disorder where modulation of G protein-coupled receptors, including G protein-coupled receptor 120, is implicated, wherein such methods include administering to a system or subject in need of such treatment an effective amount of a compound of Formula (I), or pharmaceutically acceptable salts or pharmaceutical compositions thereof, thereby treating the disease or disorder including, but not limited to, those diseases and/or disorders described herein.

In certain embodiments, a compound of Formula (I), or a pharmaceutically acceptable salt or solvate thereof, is used in the preparation of a medicament for the treatment of a disease or disorder associated with or mediated by G protein-coupled receptors. In certain embodiments, a compound of Formula (I), or a pharmaceutically acceptable salt or solvate thereof, is used in the preparation of a medicament for the treatment of a disease or disorder associated with or mediated by G protein-coupled receptor 120.

In certain embodiments, the system or subject used in the methods provided herein are cell or tissue systems. In certain embodiments, the system or subject used in the methods provided herein are human or animal subjects.

In accordance with the foregoing, provided herein are methods for preventing, treating and/or ameliorating the condition of any of the diseases or disorders described herein in a subject in need of such treatment, which method comprises administering to the subject a therapeutically effective amount of a compound of Formula (I), or a pharmaceutically acceptable salt thereof. For any of the methods and uses provided herein, the required dosage will vary depending on the mode of administration, the particular condition to be treated and the effect desired.

Routes of Administration and Pharmaceutical Compositions

For the therapeutic uses of compounds of Formula (I), or pharmaceutically acceptable salts, solvates, N-oxides, prodrugs and isomers thereof, provided herein, such compounds are administered in therapeutically effective amounts either alone or as part of a pharmaceutical composition. Accordingly, provided herein are pharmaceutical compositions, which comprise at least one compound of Formulas (I), pharmaceutically acceptable salts solvates, N-oxides, prodrugs or isomers thereof, and one or more pharmaceutically acceptable carriers, diluents, or excipients. In addition, such compounds and compositions are administered singly or in combination with one or more additional therapeutic agents. The routes of administration of compounds of Formula (I), or pharmaceutically acceptable salts, solvates, N-oxides, prodrugs or isomers thereof, and pharmaceutical compositions containing at least one compound of Formula (I) or pharmaceutically acceptable salts, solvates, N-oxides, prodrugs or isomers thereof, include, but are not limited to, oral administration, intravitreal administration, rectal administration, parenteral, intravenous administration, intraperitoneal administration, intramuscular administration, inhalation, transmucosal administration, pulmonary administration, intestinal administration, subcutaneous administration, intramedullary administration, intrathecal administration, direct intraventricular, intranasal administration, topical administration, ophthalmic administration or otic administration.

In certain embodiments, compounds of Formula (I), or pharmaceutically acceptable salts, solvates, N-oxides, prodrugs and isomers thereof, or pharmaceutical compositions containing at least one compound of Formula (I) or pharmaceutically acceptable salts, solvates, N-oxides, prodrugs or isomers thereof, are administered locally, while in other embodiments compounds of Formula (I), or pharmaceutically acceptable salts, solvates, N-oxides, prodrugs and isomers thereof, or pharmaceutical compositions containing at least one compound of Formula (I) or pharmaceutically acceptable salts, solvates, N-oxides, prodrugs or isomers thereof, are administered systemically. Local administration includes, but is not limited to, injection into an organ, optionally in a depot or sustained release formulation. Systemic administration includes, but is not limited to, oral administration or intravenous administration. In other embodiments, compounds of Formula (I), or pharmaceutically acceptable salts, solvates, N-oxides, prodrugs and isomers thereof, or pharmaceutical compositions containing at least one compound of Formula (I) or pharmaceutically acceptable salts, solvates, N-oxides, prodrugs or isomers thereof, are administered in a targeted drug delivery system, such as, by way of example only, in a liposome coated with organ-specific antibody. The liposome is targeted to and taken up selectively by the organ. In other embodiments, compounds of Formula (I), or pharmaceutically acceptable salts, solvates, N-oxides, prodrugs and isomers thereof, or pharmaceutical compositions containing at least one compound of Formula (I) or pharmaceutically acceptable salts, solvates, N-oxides, prodrugs or isomers thereof, are administered in the form of a rapid release formulation, while in other embodiments, they are administered in the form of an extended release formulation. In other embodiments, compounds of Formula (I), or pharmaceutically acceptable salts, solvates, N-oxides, prodrugs and isomers thereof, or pharmaceutical compositions containing at least one compound of Formula (I) or pharmaceutically acceptable salts, solvates, N-oxides, prodrugs or isomers thereof, are administered in the form of an intermediate release formulation.

The therapeutically effective amount will vary depending on, among others, the disease indicated, the severity of the disease, the age and relative health of the subject, the potency of the compound administered, the route of administration and the treatment desired. In certain embodiments, satisfactory results are indicated to be obtained at daily dosages of a compound of Formula (I) from about 0.01 to 2.5 mg/kg per body weight. In certain embodiments, the daily dosage of a compound of Formula (I), administered orally, is in the range from about 0.01 to 50 mg/kg per body weight. By way of example only, a compound of Formula (I) (as an active ingredient) is orally administered to a patient with hyperlipidemia in about 0.01 to about 30 mg/kg of body weight per day; in other examples, from about 0.1 to about 20 mg/kg of body weight per day; and in still other examples, from about 1 to about 20 mg/kg of body weight per day, which is given at once or in several portions per day.

In certain embodiments, the daily dosage of a compound of Formula (I), administered topically, is in the range from 0.05 micrograms per kilogram body weight (μg/kg) to 100 micrograms per kilogram body weight (μg/kg). In other embodiments, the daily dosage of a compound of Formula (I), administered parenterally, is in the range from 0.05 micrograms per kilogram body weight (μg/kg) to 100 milligrams per kilogram body weight (mg/kg). In certain embodiments, the daily dosage of a compound of Formula (I), administered intrermuscularlly, is in the range from 0.05 micrograms per kilogram body weight (μg/kg) to 100 micrograms per kilogram body weight (μg/kg). An indicated daily dosage in the larger mammal, e.g. humans, is in the range from about 0.01 mg/kg to about 100 mg/kg of a compound of Formula (I), conveniently administered, e.g. in divided doses up to four times a day or in controlled release form. In certain embodiment, unit dosage forms for oral administration comprise from about 1 to 50 mg of a compound of Formula (I).

Provided herein are processes for the preparation of pharmaceutical compositions comprising at least one compound of Formula (I). In certain embodiments, such processes include admixing a compound of Formula (I) with one or more pharmaceutically acceptable carriers, diluents or excipients. In certain embodiments, the pharmaceutical compositions comprise a compound of Formula (I) in free form or in a pharmaceutically acceptable salt or solvate form. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, dissolving, granulating dragee-making, levigating, emulsifying, encapsulating, entrapping or compression processes and/or coating methods. In other embodiments, such compositions are optionally contain excipients or adjuvants, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, pills, dragees, granules, liquids, gels, syrups, flavored syrups, elixirs, slurries, solutions or suspensions in aqueous or non-aqueous liquids, edible foams or whips, and oil-in-water liquid emulsions or water-in-oil liquid emulsions. The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (such as, by way of example only, granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compound of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, aqueous isotonic solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, physiological saline buffer, Ringer's Injection solution, Dextrose Injection, Dextrose and Sodium Chloride Injection, and Lactated Ringer's Injection solution; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments, a compound of Formula (I) or composition containing one or more compounds of Formula (I) is parenteral administration by bolus injection. In other embodiments, a compound of Formula (I) or composition containing one or more compounds of Formula (I) is parenteral administration by continuous infusion. Formulations for injection are presented in unit dosage form, by way of example only, in ampoules or formulations for injection are presented in multi-dose containers, with an added preservative. The compositions may take such forms as suspensions, solutions or emulsions in oily or aqueous vehicles, and may contain formulatory agents such as suspending, stabilizing and/or dispersing agents.

Transdermal Administration

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used. In certain embodiments transdermal administration is used to provide continuous, while in other embodiments transdermal administration is used to provide discontinuous infusion of a compound of Formula (I) in controlled amounts.

In certain embodiments, the rate of absorption is slowed by using rate-controlling membranes or by trapping the compound within a polymer matrix or gel. In certain embodiments, transdermal delivery is via a transdermal patch.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compound of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compound of Formula (I) are used to further adjust the properties of the resulting composition.

In other embodiments, transdermal delivery of the compound of Formula (I) is accomplished by means of iontophoretic patches and the like Topical Dosage Forms In certain embodiments at least one compound of Formula (I) is administered by topical application to the skin or eyes of a pharmaceutical composition containing at least one compound of Formula (I) in the form of lotions, gels, ointments solutions, emulsions, aqueous solutions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Pulmonary Administration

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compound of Formula (I) are be administered directly to the lung by inhalation using a Metered Dose Inhaler ("MDI"), which utilizes canisters that contain a suitable low boiling propellant, such as, by way of example only, dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compound of Formula (I) are delivered to the lung using a liquid spray device, wherein such devices use extremely small nozzle holes to aerosolize liquid drug formulations that can then be directly inhaled into the lung. In other embodiments, compound of Formula (I) are delivered to the lung using a nebulizer device, wherein a nebulizers creates an aerosols of liquid drug formulations by using ultrasonic energy to form fine particles that can be readily inhaled. In other embodiments, compound of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

Rectal Administration

In certain embodiments pharmaceutical compositions containing at least one compound of Formula (I) are administered rectally in the form of suppositories, enemas, retention enemas ointment, creams rectal foams or rectal gels. In certain embodiments such suppositories are prepared from fatty emulsions or suspensions, cocoa butter or other glycerides.

Depot Administration

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In certain embodiments injectable depot forms are made by forming microencapsulated matrices of the compound of Formula (I) in biodegradable polymers. The rate of compound of Formula (I) release is controlled by varying the ratio of compound of Formula (I) to polymer and the nature of the particular polymer employed. In other embodiments, depot injectable formulations are prepared by entrapping the compound of Formula (I) in liposomes or microemulsions.

Ophthalmic Administration

In certain embodiments, a compound of Formula (I) or pharmaceutical composition described herein are ophthalmically administered to the eye. Administration to the eye generally results in direct contact of the agents with the cornea, through which at least a portion of the administered agents pass. In certain embodiments, such compounds of Formula (I) or pharmaceutical compositions have an effective residence time in the eye of about 2 to about 24 hours. In certain embodiments, such compounds of Formula (I) or pharmaceutical compositions have an effective residence time in the eye of about 4 to about 24 hours. In certain embodiments, such compounds of Formula (I) or pharmaceutical compositions have an effective residence time in the eye of about 6 to about 24 hours.

Ophthalmic administration, as used herein, includes, but is not limited to, topical administration, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the formix). In certain embodiments, the compounds of Formula (I) or pharmaceutical composition described herein are formulated as an ophthalmic composition and are administered topically to the eye. Such topically administered ophthalmic compositions include, but are not limited to, solutions, suspensions, gels or ointments.

In certain embodiments the pharmaceutical compositions, comprising at least one compound of Formula (I) described herein, used for ophthalmic administration take the form of a liquid where the compositions are present in solution, in suspension or both. In some embodiments, a liquid composition includes a gel formulation. In other embodiments, the liquid composition is aqueous. In other embodiments, such liquid compositions take the form of an ointment. In certain embodiments pharmaceutical compositions containing at least one compound of Formula (I) are administered ophthalmically as eye drops formulated as aqueous solutions that optionally contain solubilizers, stabilizers, tonicity enhancing agents, buffers and preservatives. A desired dosage is administered via a known number of drops into the eye. By way of example only, for a drop volume of 25 administration of 1-6 drops delivers 25-150 µl of the composition. In certain embodiments, the aqueous compositions contain from about 0.01% to about 50% weight/volume of a compound of Formula (I). In other embodiments, the aqueous compositions contain from about 0.1% to about 20% weight/volume of a compound of Formula (I). In still other embodiments, the aqueous compositions contain from about 0.2% to about 10% weight/volume of a compound of Formula (I). In certain embodiments, the aqueous compositions contain from about 0.5% to about 5%, weight/volume of a compound of Formula (I).

In certain embodiments the aqueous compositions have an ophthalmically acceptable pH and osmolality. In certain embodiments the aqueous compositions include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

In certain embodiments the compositions also include also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments the aqueous compositions also contain one or more polymers as suspending agents. Such polymers include, but are not limited to, water-soluble polymers such as cellulosic polymers described herein, (for example only, hydroxypropyl methylcellulose), and water-insoluble polymers described herein (for example only, cross-linked carboxyl-containing polymers). In certain embodiments, the aqueous compositions also include an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In certain embodiments the compositions also include ophthalmically acceptable solubilizing agents to aid in the solubility of a compound of Formula (I). The term "solubilizing agent" generally includes agents that result in formation of a micellar solution or a true solution of the agent. In certain embodiments, ophthalmically acceptable nonionic surfactants including, but not limited to, polysorbate 80 are used as solubilizing agents. In other embodiments, ophthalmically acceptable glycols including, but not limited to, polyglycols, polyethylene glycol 400, and glycol ethers are used as solubilizing agents.

In certain embodiments the compositions also include one or more ophthalmically acceptable surfactants to enhance physical stability or for other purposes. Such nonionic surfactants include, but are not limited to, polyoxyethylene fatty acid glycerides and vegetable oils (by way of example only, polyoxyethylene (60) hydrogenated castor oil) and polyoxyethylene alkylethers and alkylphenyl ethers (by way of example only, octoxynol 10 and octoxynol 40).

In certain embodiments the compositions also include one or more ophthalmically acceptable preservatives to inhibit microbial activity. Such preservatives include, but are not limited to mercury-containing substances such as merfen and thiomersal; stabilized chlorine dioxide; and quaternary ammonium compounds such as benzalkonium chloride, cetyltrimethylammonium bromide and cetylpyridinium chloride.

In certain embodiments the compositions also include one or more antioxidants to enhance chemical stability where required. Such antioxidants include, but are not limited to, ascorbic acid and sodium metabisulfite.

In certain embodiments, the aqueous compositions provided herein are packaged in single-dose non-reclosable containers, while in other embodiments the aqueous compositions provided herein are packaged in multiple-dose reclosable containers wherein a preservative is included in the composition.

Otic Administration

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In a further embodiment, pharmaceutical compositions comprising at least one compound of Formula (I) are adapted for oral administration for the treatment of metabolic diseases and/or disorders. In a further embodiment, pharmaceutical compositions comprising at least one compound of Formula (I) are adapted for oral administration for the treatment of diabetes. In a further embodiment, pharmaceutical compositions comprising at least one compound of Formula (I) are adapted for oral administration for the treatment of obesity. In a further embodiment, pharmaceutical compositions comprising at least one compound of Formula (I) are adapted for oral administration for the treatment of systematic lupus erythematosus (SLE).

In a further embodiment, pharmaceutical compositions comprising at least one compound of Formula (I) are adapted for oral administration for the treatment of respiratory diseases. In a further embodiment, pharmaceutical compositions comprising at least one compound of Formula (I) are adapted for oral administration for the treatment of asthma. In a further embodiment, pharmaceutical compositions comprising at least one compound of Formula (I) are adapted for oral administration for the treatment of rhinitis. In a further embodiment, pharmaceutical compositions comprising at least one compound of Formula (I) are adapted for oral administration for the treatment of COPD.

Combination Therapies

The compounds of Formula (I) provided herein are administered in therapeutically effective amounts either singly or in combination with one or more therapeutic agents via any of the routes of administration provided herein. In certain embodiments, compounds of Formula (I) are mixed with the other therapeutic agent in a fixed pharmaceutical composition, or are administered separately, either before, simultaneously with or after the other therapeutic agent.

In certain embodiments, a compound of Formulas (I) described herein, or a pharmaceutically acceptable salt or solvate thereof, or a pharmaceutical composition containing at least one compound of Formula (I), is administered alone (without an additional therapeutic agent) for the prevention and/or treatment of one or more of the disease and/or disorders associated with or mediated by G protein-coupled receptor 120 (GPR120) described herein.

In other embodiments, a compound of Formulas (I) described herein, or a pharmaceutically acceptable salt or solvate thereof, or a pharmaceutical composition containing at least one compound of Formula (I), is formulated in combination with one or more additional therapeutic agents and administered for the prevention and/or treatment of one or more of the disease and/or disorders associated with or mediated by G protein-coupled receptor 120 (GPR120) described herein.

In other embodiments, a compound of Formulas (I) described herein, or a pharmaceutically acceptable salt or solvate thereof, or a pharmaceutical composition containing at least one compound of Formula (I), is administered in combination with one or more additional therapeutic agents, for the prevention and/or treatment of one or more of the disease and/or disorders associated with or mediated by G protein-coupled receptor 120 (GPR120) described herein.

In other embodiments, a compound of Formulas (I) described herein, or a pharmaceutically acceptable salt or solvate thereof, or a pharmaceutical composition containing at least one compound of Formula (I), is administered sequentially with one or more additional therapeutic agents, for the prevention and/or treatment of one or more of the disease and/or disorders associated with or mediated by G protein-coupled receptor 120 (GPR120) described herein.

In other embodiments, the combination treatments provided herein include administration of a compound of Formula (I) described herein, or a pharmaceutically acceptable salt or solvate thereof, or a pharmaceutical composition containing a compound of Formula (I), prior to administration of one or more additional therapeutic agents, for the prevention and/or treatment of one or more of the disease and/or disorders associated with or mediated by G protein-coupled receptor 120 (GPR120) described herein.

In other embodiments, the combination treatments provided herein include administration of a compound of Formula (I) described herein, or a pharmaceutically acceptable salt or solvate thereof, or a pharmaceutical composition containing a compound of Formula (I), subsequent to administration of one or more additional therapeutic agents, for the prevention and/or treatment of one or more of the disease and/or disorders associated with or mediated by G protein-coupled receptor 120 (GPR120) described herein.

In certain embodiments, the combination treatments provided herein include administration of a compound of Formula (I) described herein, or a pharmaceutically acceptable salt or solvate thereof, or a pharmaceutical composition containing a compound of Formula (I), concurrently with one or more additional therapeutic agents, for the prevention and/or treatment of one or more of the disease and/or disorders associated with or mediated by G protein-coupled receptor 120 (GPR120) described herein.

In certain embodiments of the combination treatments described herein the compounds of Formula (I), or a pharmaceutically acceptable salts or solvates thereof, are modulators of G protein-coupled receptors. In certain embodiments of the combination treatments described herein the compounds of Formula (I), or a pharmaceutically acceptable salts or solvates thereof, are modulators of G protein-coupled receptor 120. In certain embodiments of the combination treatments described herein the compounds of Formula (I), or a pharmaceutically acceptable salts or solvates thereof, are agonists of G protein-coupled receptors. In certain embodiments of the combination treatments described herein the compounds of Formula (I), or a pharmaceutically acceptable salts or solvates thereof, are agonists of G protein-coupled receptor 120. In certain embodiments of the combination treatments described herein the compounds of Formula (I), or a pharmaceutically acceptable salts or solvates thereof, are antagonists of G protein-coupled receptors. In certain embodiments of the combination treatments described herein the compounds of Formula (I), or a pharmaceutically acceptable salts or solvates thereof, are antagonists of G protein-coupled receptor 120.

In certain embodiments of the combination therapies described herein, the compounds of Formula (I) described herein, or a pharmaceutically acceptable salts or solvates thereof, and the additional therapeutics agent(s) act additively. In certain embodiments of the combination therapies described herein, the compounds of Formula (I) described herein, or a pharmaceutically acceptable salts or solvates thereof, and the additional therapeutics agent(s) act synergistically.

In other embodiments, a compound of Formula (I) described herein, or a pharmaceutically acceptable salts or solvates thereof, or a pharmaceutical composition containing a compound of Formula (I), is administered to a patient who has not previously undergone or is not currently undergoing treatment with another therapeutic agent.

In certain embodiments, the compounds of Formula (I) provided herein are used in combination with other therapeutic substances such as therapeutic agents for treating diabetes, diabetic complications, dyslipidemia, hyperlipidemia, antihypertensive agents, antiobesity agents, diuretics, chemotherapeutic agents, immunotreating agents, immunomodulators, anti-inflammatory agents, antithrombotic agents, therapeutic agents for osteoporosis, antibacterial agents, antifungal agents, antiprotozoal agents, antibiotics, antitussives and expectorant drugs, sedatives, anesthetics, antiulcer agents, tranquilizers, antipsychotic agents, antitumor agents, muscle relaxants, antiepileptics, antidepressants, antiallergic agents, cardiac stimulants, antiarrhythmic agents, vasodilators, vasoconstrictors, narcotic antagonists, vitamins, vitamin derivatives, antiasthmatic agents, antidementia agents, treating agents for pollakiuria or urinary incontinence, therapeutic agents for dysuria, treating agents for atopic dermatitis, therapeutic agents for allergic rhinitis, vasopressors, endotoxin antagonists or antibodies, signal transduction inhibitors, inflammatory mediator effect suppressants, inflammatory mediator effect suppressing antibodies, anti-inflammatory mediator effect suppressants, anti-inflammatory mediator effect suppressing antibodies and the like.

Therapeutic agents for diabetes used in combination with at least one compound of Formula (I) include, but are not limited to, insulin preparations (such as, by way of example only, animal insulin preparations extracted from pancreas of bovine or pig; human insulin preparations genetically synthesized using Escherichia coli or yeast; zinc insulin; protamine zinc insulin; fragment or derivative of insulin (such as, by way of example only, INS-1), oral insulin preparation and the like), insulin sensitizers (such as, by way of example only, pioglitazone or a salt thereof (including the hydrochloride salt), troglitazone, rosiglitazone or a salt thereof (including the maleate salt), Reglixane (JTT-501), Netoglitazone (MCC-555), YM-440, GI-262570, KRP-297, FK-614, CS-011, (E)-1-[[[4-[(5-methyl-2-phenyl-4-oxazolyfl-methoxy]phenyl]methoxy]imino]benzenebutanoic acid and the like, compounds described in WO 99/58510 (such as, by way of example only, (E)-4-[4-(5-methyl-2-phenyl-4-oxazolylmethoxy)-benzyloxyimino]-4-phenylbutyric acid), compounds described in WO 01/38325, Tesaglitazar (AZ-242), Ragaglitazar (N,N-622), BMS-298585, ONO-5816, BM-13-1258, LM-4156, MBX-102, LY-519818, MX-6054, LY-510929, Balaglitazone (N,N-2344), T-131 or a salt thereof, THR-0921), -glucosidase inhibitors (such as, by way of example only, voglibose, acarbose, miglitol and emiglitate), biguanides (such as, by way of example only, phenformin, metformin, buformin), insulin secretagogues (including sulfonylurea (such as, by way of example only, tolbutamide, glibenclamide, gliclazide, chlorpropamide, tolazamide, acetohexamide, glyclopyramide and glimepiride), repaglinide, senaglinide, mitiglinide or calcium salt hydrate thereof and nateglinide), GLP-1 receptor agonists (such as, by way of example only, GLP-1, GLP-1MR agent, N,N-2211, AC-2993 (exendin-4), BIM-51077, Aib(8,35) hGLP-1(7,37)NH2, CJC-1131), dipeptidyl peptidase IV inhibitors (such as, by way of example only, NVP-DPP-278, PT-100, P32/98, P93/01, NVP-DPP-728, LAF237 and TS-021), beta-3-agonists (such as, by way of example only, CL-316243, SR-58611-A, UL-TG-307, AJ-9677 and AZ40140), amylin agonists (such as, by way of example only, pramlintide), phosphotyrosine phosphatase inhibitors (such as, by way of example only, vanadic acid), gluconeogenesis inhibitors (such as, by way of example only, glycogen phosphorylase inhibitors, glucose-6-phosphatase inhibitors, glucagon antagonists), SGLT (sodium-glucose cotransporter) inhibitors (such as, by way of example only, T-1095), 11-hydroxysteroid dehydrogenase inhibitors (such as, by way of example only, BVT-3498), adiponectin or agonists thereof, IKK inhibitors (such as, by way of example only, AS-2868), leptin resistance improving drugs, somatostatin receptor agonists (compounds described in WO 01/25228, WO 03/42204, compounds described in WO 98/44921, WO 98/45285, WO 99/22735, etc.), glucokinase activators (such as, by way of example only, Ro-28-1675) and the like.

Therapeutic agents for treating diabetic complications used in combination with at least one compound of Formula (I) include, but are not limited to, aldose reductase inhibitors (such as, by way of example only, Tolrestat, Epalrestat, Zenarestat, Zopolrestat, Fidarestat (SNK-860), Minalrestat (ARI-509) and CT-112), neurotrophic factors and increasing drugs thereof (such as, by way of example only, NGF, NT-3, BDNF, neurotrophin production-secretion promoters described in WO 01/14372 (such as, by way of example only, 4-(4-chlorophenyl)-2-(2-methyl-1-imidazolyl)-5-[3-(2-methylphenoxy)propyl]oxazole and the like), protein kinase C (PKC) inhibitors (such as, by way of example only, LY-333531), AGE inhibitors (such as, by way of example only, ALT-945, pimagedine, pyratoxanthine, N-phenacylthiazolium bromide (ALT-766), EXO-226, ALT-711, Pyridorin and Pyridoxamine), active oxygen scavengers (such as, by way of example only, thioctic acid), cerebral vasodilators (such as, by way of example only, tiapuride), somatostatin receptor agonist (BIM23190), apoptosis signal regulating kinase-1 (ASK-1) inhibitors and the like.

Therapeutic agents for treating hyperlipidemia used in combination with at least one compound of Formula (I) include, but are not limited to, statin compounds which are cholesterol synthesis inhibitors (such as, by way of example only, pravastatin, simvastatin, lovastatin, atorvastatin, fluvastatin, cerivastatin or a salt thereof (such as, by way of example only, sodium salt), squalene synthase inhibitors (such as, by way of example only, compounds described in WO 97/10224, such as N-[[(3R,55)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (such as, by way of example only, bezafibrate, clofibrate, simfibrate and clinofibrate), antioxidants (such as, by way of example only, lipoic acid and probucol).

Antihypertensive agents used in combination with at least one compound of Formula (I) include, but are not limited to, angiotensin converting enzyme inhibitors (such as, by way of example only, captopril, enalapril and delapril), angiotensin II antagonists (such as, by way of example only, losartan, candesartan, cilexetil, eprosartan, valsartan, telmisartan, irbesartan, tasosartan and 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (such as, by way of example only, manidipine, nifedipine, amlodipine, efonidipine and nicardipine), clonidine and the like.

Antiobesity agents used in combination with at least one compound of Formula (I) include, but are not limited to, antiobesity agents acting on the central nervous system (such as, by way of example only, dexfenfluramine, fenfluramine, phentermine, sibutramine, amfepramone, dexamphetamine, mazindol, phenylpropanolamine, clobenzorex; MCH receptor antagonists (such as, by way of example only, SB-568849; SNAP-7941; compounds encompassed in WO 01/82925 and WO 01/87834); neuropeptide Y antagonists (such as, by way of example only, CP-422935); cannabinoid receptor antagonists (such as, by way of example only, SR-141716 and SR-147778); ghrelin antagonists; 11-hydroxysteroid dehydrogenase inhibitors (such as, by way of example only, BVT-3498) and the like), pancreatic lipase inhibitors (such as, by way of example only, orlistat and ATL-962), beta-3-agonists (such as, by way of example only, CL-316243, SR-58611-A, UL-TG-307, AJ-9677 and AZ40140), peptide anorexiants (such as, by way of example only, leptin and Ciliary Neurotropic Factor (CNTF)), cholecystokinin agonists (such as, by way of example only, lintitript and FPL-15849), feeding deterrent (such as, by way of example only, P-57) and the like.

Diuretics used in combination with at least one compound of Formula (I) include, but are not limited to, xanthine derivatives (such as, by way of example only, theobromine sodium salicylate and theobromine calcium salicylate), thiazide preparations (such as, by way of example only, ethiazide, cyclopenthiazide, trichloromethiazide, hydrochlorothiazide, hydroflumethiazide, benzyl hydrochlorothiazide, penflutizide, polythiazide and methyclothiazide), antialdosterone preparations (such as, by way of example only, spironolactone and triamterene), carbonate dehydratase inhibitors (such as, by way of example only, acetazolamide and the like), chlorobenzenesulfonamide preparations (such as, by way of example only, chlorthalidone, mefruside and indapamide), azosemide, isosorbide, ethacrynic acid, piretanide, bumetanide, furosemide and the like.

Chemotherapeutic agents or other anti-proliferative agents used in combination with at least one compound of Formula (I) include, but are not limited to, alkylating agents (such as, by way of example only, cyclophosphamide and ifosfamide), metabolic antagonists (such as, by way of example only, methotrexate and 5-fluorouracil), antitumor antibiotics (such as, by way of example only, mitomycin and adriamycin), plant-derived antitumor agent (such as, by way of example only, vincristine, vindesine and Taxol), cisplatin, carboplatin, etoposide and the like.

Other chemotherapeutic agents or other anti-proliferative agents used in combination with at least one compound of Formula (I) include, but are not limited to, surgery, radiotherapy (gamma.-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™, adriamycin, dexamethasone, and cyclophosphamide.

Immunotreating agents used in combination with at least one compound of Formula (I) include, but are not limited to, microorganism or bacterial components (such as, by way of example only, muramyl dipeptide derivative and Picibanil), polysaccharides having immunity potentiating activity (such as, by way of example only, lentinan, schizophyllan and krestin), cytokines obtained by genetic engineering techniques (such as, by way of example only, interferon and interleukins (IL) (including IL-1, IL-2, IL-12 and the like), colony stimulating factors (such as, by way of example only, granulocyte colony stimulating factor and erythropoietin) and the like.

The immunomodulatory agents used in combination with at least one compound of Formula (I) described herein, or a pharmaceutically acceptable salt or solvate thereof, include, but are not limited to, azathioprine, tacrolimus, cyclosporine, antimalarials, methothrexate, leflunomide, corticosteroids, cyclophosphamide, cyclosporin A, cyclosporin G, mycophenolate mofetil, ascomycin, rapamycin (sirolimus), FK-506, mizoribine, 15-deoxyspergualin, brequinar, mycophenolic acid, malononitriloamindes (such as, by way of example only, leflunamide), CTLA4Ig, T cell receptor modulators, and cytokine receptor modulators, peptide mimetics, and antibodies (such as, by way of example only, human, humanized, chimeric, monoclonal, polyclonal, Fvs, ScFvs, Fab or F(ab)$_2$ fragments or epitope binding fragments), nucleic acid molecules (such as, by way of example only, antisense nucleic acid molecules and triple helices), small molecules, organic compounds, and inorganic compounds. Examples of monoclonal antibodies include, but are not limited to, monoclonal antibodies for leukocyte receptors such as, by way of example only MHC, CD2, CD3, CD4, CD7, CD25, CD28, B7, CD45, CD58 or their ligands. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Hex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, toll-like receptor (TLR) modulators. Examples of cytokine receptor modulators include, but are not limited to, soluble cytokine receptors (such as, by way of example only, the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-.alpha., interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-antibodies, anti-IL-1β antibodies, anti-IL-6 antibodies, anti-IL-8 antibodies (such as, by way of example only, ABX-IL-8 (Abgenix)), and anti-IL-12 antibodies).

Anti-inflammatory agents used in combination with at least one compound of Formula (I) include, but are not limited to, non-steroidal anti-inflammatory agents (such as, by way of example only, salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide); leukotriene antagonists including, but not limited to, zileuton, aurothioglucose, gold sodium thiomalate and auranofin; steroids including, but not limited to, alclometasone diprorionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

Antithrombotic agents used in combination with at least one compound of Formula (I) include, but are not limited to, heparin (such as, by way of example only, heparin sodium, heparin calcium and dalteparin sodium), warfarin (such as, by way of example only, warfarin potassium), antithrombin drugs (such as, by way of example only, aragatroban), thrombolytic agents (such as, by way of example only, urokinase, tisokinase, alteplase, nateplase, monteplase and pamiteplase), platelet aggregation suppressors (such as, by way of example only, ticlopidine hydrochloride, cilostazol, ethyl icosapentate, beraprost sodium and sarpogrelate hydrochloride) and the like.

Therapeutic agents for treating osteoporosis used in combination with at least one compound of Formula (I) include, but are not limited to, alfacalcidol, calcitriol, elcatonin, calcitonin salmon, estriol, ipriflavone, pamidronate disodium, alendronate sodium hydrate, incadronate disodium and the like.

Vitamins used in combination with at least one compound of Formula (I) include, but are not limited to, vitamin B1, vitamin B12 and the like, and derivatives thereof.

Antidementia agents used in combination with at least one compound of Formula (I) include, but are not limited to, tacrine, donepezil, rivastigmine, galantamine and the like.

Therapeutic agents for pollakiuria or urinary incontinence used in combination with at least one compound of Formula (I) include, but are not limited to, flavoxate hydrochloride, oxybutynin hydrochloride, propiverine hydrochloride and the like.

Therapeutic agents for dysuria used in combination with at least one compound of Formula (I) include, but are not limited to, acetylcholine esterase inhibitors (such as, by way of example only, distigmine) and the like.

Therapeutic agents having a cachexia-improving effect in animal models and clinical situations used in combination with at least one compound of Formula (I) include, but are not limited to, cyclooxygenase inhibitors (such as, by way of example only, indomethacin), progesterone derivatives (such as, by way of example only, megestrol acetate), glucosteroids (such as, by way of example only, dexamethasone), metoclopramide agents, tetrahydrocannabinol agents, fat metabolism improving agents (such as, by way of example only, eicosapentanoic acid), growth hormones, IGF-1, or antibodies to a cachexia-inducing factor such as TNF-, LIF, IL-6, oncostatin M and the like.

Glycosylation inhibitors used in combination with at least one compound of Formula (I) include, but are not limited to, ALT-711, nerve regeneration promoting drugs (such as, by way of example only, Y-128, VX853 and prosaptide), antidepressants (such as, by way of example only, desipramine, amitriptyline and imipramine), antiepileptics (such as, by way of example only, lamotrigine, Trileptal, Keppra, Zonegran, Pregabalin, Harkoseride and carbamazepine), antiarrhythmic agents (such as, by way of example only, mexiletine), acetylcholine receptor ligands (such as, by way of example only, ABT-594), endothelin receptor antagonists (such as, by way of example only, ABT-627), monoamine uptake inhibitors (such as, by way of example only, tramadol), narcotic analgesics (such as, by way of example only, morphine), GABA receptor agonists (such as, by way of example only, gabapentin, gabapentin MR preparations), 2 receptor agonists (such as, by way of example only, clonidine), local analgesics (such as, by way of example only, capsaicin), antianxiety drugs (such as, by way of example only, benzodiazepines), phosphodiesterase inhibitors (such as, by way of example only, sildenafil), dopamine receptor agonists (such as, by way of example only, apomorphine) and the like.

In certain embodiments, the additional therapeutic agent(s) used in the combination therapies described herein include, but are not limited to, agents such as tumour necrosis factor alpha (TNF-α) inhibitors (such as anti-TNF monoclonal antibodies (by way of example only, Remicade, CDP-870 and adalimumab) and TNF receptor immunoglobulin molecules (by way of example only, Enbrel, Remicade, and Humira)); non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

Kits

Provided herein are kits of a pharmaceutical combinations, comprising a) a first agent comprising a compound of Formula I, (Formula (Ia), (Ib), (Ic) or (Id)), in free form or in pharmaceutically acceptable salt form, and b) at least one co-therapeutic agent. In certain embodiments, the kit further comprises instructions for administration of the pharmaceutical composition.

In other aspects provided herein are pharmaceutical packs or kits that include one or more containers containing a compound of Formula (I) useful for the treatment or prevention of a disease or disorder associated with or mediated by G protein-coupled receptors. In other embodiments, such pharmaceutical packs or kits include one or more containers containing a compound of Formula (I) useful for the treatment or prevention of a disease or disorder associated with or mediated by G protein-coupled receptors and one or more containers containing an additional therapeutic agent, including but not limited to those listed above. In certain embodiments, such pharmaceutical packs or kits optionally include instructions for administration of a compound of Formula (I).

EXAMPLES

The following examples are offered to illustrate, but not to limit, the compounds of Formula (I) provided herein, and the preparation of such compounds.

Example 1

(Z)-4-(3-ethyl-4-(2-methoxyphenyl)thiazol-2(3H)-ylideneamino)benzenesulfonic acid

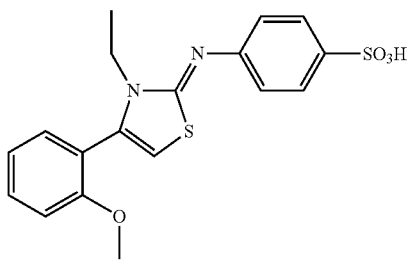 [SMILES: CCn1c(-c2ccccc2OC)cs/c1=N\c1ccc(S(=O)(=O)O)cc1]

(Z)-4-(3-ethyl-4-(2-methoxyphenyl)thiazol-2(3H)-ylideneamino)benzenesulfonic acid (1-5) is synthesized in three steps as shown in reaction scheme 1.

Scheme 1

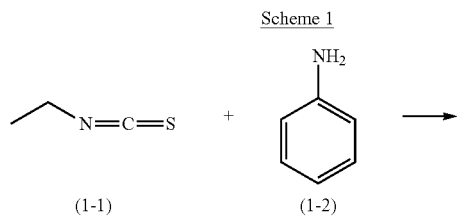

(1-1)    (1-2)

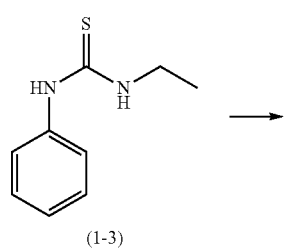

(1-3)

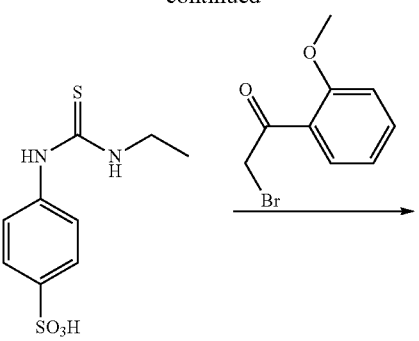

(1-4)

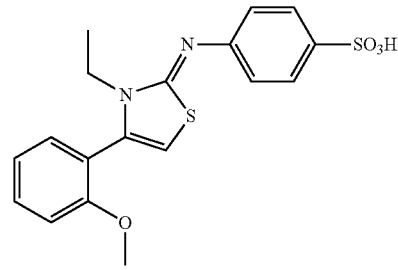

(1-5)

Example 1a 1-ethyl-3-phenylthiourea (1-3)

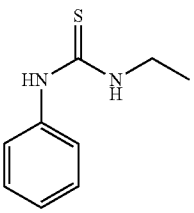

A solution of ethyl isothiocyanate (1-1) (652 mg, 7.5 mmol) and aniline (1-2) (465 mg, 5.0 mmol) in acetonitrile (5 mL) is heated to 80° C. for 14 hours. After cooling to room temperature, the mixture is poured into water (50 mL) and extracted with ethyl acetate (EtOAc) (3×50 mL). The combined organic layers are washed with brine and dried using MgSO$_4$. The drying agents are removed by filtration and the solvent is removed under vacuum. The resulting residue is then purified by flash column chromatography (silica gel, EtOAc/hexane, 0%~40%) to provide 1-ethyl-3-phenylthiourea (1-3) as a white powder. HPLC-MS calculated for $C_9H_{12}N_2S$ (M+H$^+$) 181.1. found 181.1.

Example 1b 4-(3-ethylthioureido)benzenesulfonic acid (1-4)

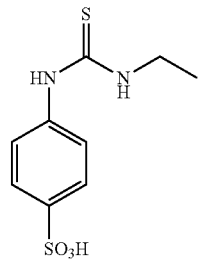 [SMILES: CCNC(=S)Nc1ccc(S(=O)(=O)O)cc1]

A solution of chlorosulfanic acid (3 mL) is cooled to 0° C. and 1-ethyl-3-phenylthiourea (360 mg, 2.0 mmol) is then added over a period of 5 minutes and the resulting mixture is stirred at 0° C. for 2 hour followed by addition of water (10 mL) which results in the formation of a precipitate. EtOAc is added to dissolve the precipitate and the mixture is extracted (5×15 mL). The combined organic layers are concentrated and dissolved in a mixture of dioxane and water (12 mL, 1:1). The resulted mixture is heated to 80° C. for 2 hr. and concentrated to provide 4-(3-ethylthioureido)benzenesulfonic acid (1-4) as an off white solid. HPLC-MS calculated for $C_9H_{12}N_2O_3S_2$ (M+H$^+$) 261.0. found 261.0.

Example 1c (Z)-4-(3-ethyl-4-(2-methoxyphenyl)thiazol-2(3H)-ylideneamino)benzenesulfonic acid (1-5)

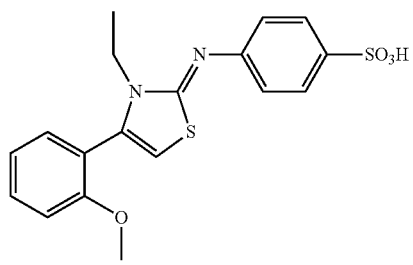 [SMILES: CCn1c(-c2ccccc2OC)cs/c1=N\c1ccc(S(=O)(=O)O)cc1]

A solution of 4-(3-ethylthioureido)benzenesulfonic acid (1-4) (50 mg, 0.19 mmol) and 2-bromo-1-(2-methoxyphenyl)ethanone (30 mg, 0.13 mmol) in MeOH (1 mL) is heated to 80° C. for 1 hour and then cooled to room temperature and concentrated. The residual is purified by preparative LC/MS to provide (Z)-4-(3-ethyl-4-(2-methoxyphenyl)thiazol-2 (3H)-ylideneamino)benzenesulfonic acid (1-5) as white solid. HPLC-MS calculated for $C_{18}H_{18}N_2O_4S_2$ (M+H$^+$) 391.1. found 391.1.

Example 2

(Z)-4-(3-ethyl-4-phenylthiazol-2(3H)-ylideneamino)benzoic acid

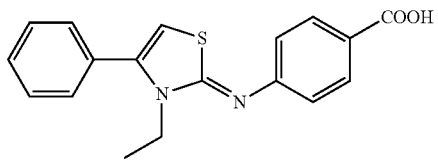 [SMILES: CCn1c(-c2ccccc2)cs/c1=N\c1ccc(C(=O)O)cc1]

(Z)-4-(3-ethyl-4-phenylthiazol-2(3H)-ylideneamino)benzoic acid (2-5) is synthesized in three steps as shown in reaction scheme 2.

Scheme 2

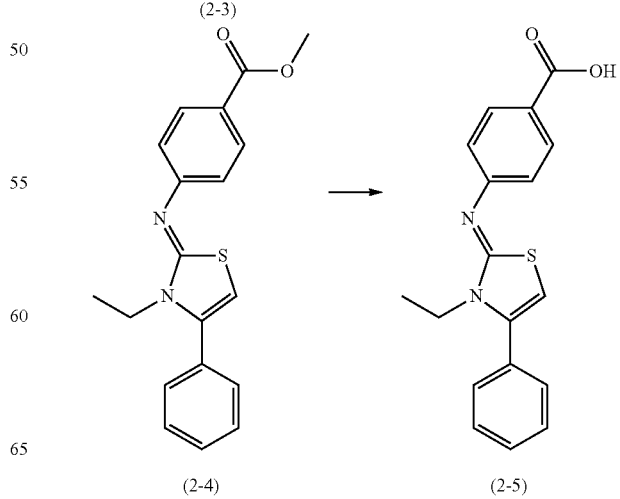

Example 2a methyl 4-(3-ethylthioureido)benzoate (2-3)

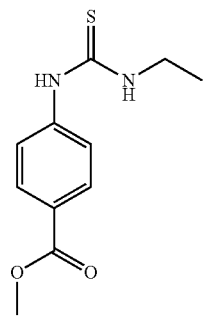 [SMILES: CCNC(=S)Nc1ccc(C(=O)OC)cc1]

To a solution of methyl 4-aminobenzoate (2-2) (30.2 mg, 0.20 mmol) in anhydrous acetonitrile (0.4 mL) is added ethyl isothiocyanate (2-1) (17.52 μL, 0.20 mmol) and the reaction mixture is heated at 80° C. overnight. After cooling to room temperature, the mixture is poured into water (50 mL) and extracted with ethyl acetate (EtOAc) (3×50 mL). The combined organic layers are washed with brine and dried using MgSO$_4$. The drying agents are removed by filtration and the solvent is removed under vacuum. The resulting residue is then purified by flash column chromatography (silica gel, EtOAc/hexane, 0%-40%) to provide methyl 4-(3-ethylthioureido)benzoate (2-3).

Example 2b (Z)-methyl 4-(3-ethyl-4-phenylthiazol-2(3H)-ylideneamino)benzoate (2-4)

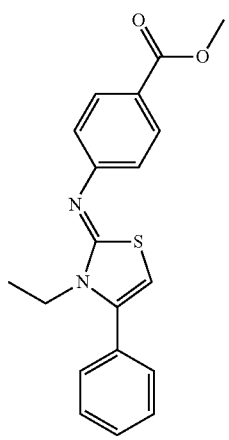 [SMILES: CCn1c(-c2ccccc2)cs/c1=N\c1ccc(C(=O)OC)cc1]

A solution of methyl 4-(3-ethylthioureido)benzoate (2-3) (50 mg, 0.19 mmol) and 2-bromoacetophenone (39.8 mg, 0.20 mmol) in MeOH (1 mL) is heated to 80° C. for 2 hours and then cooled to room temperature and concentrated to provide (Z)-methyl 4-(3-ethyl-4-phenylthiazol-2(3H)-ylideneamino)benzoate (2-4).

Example 2c (Z)-4-(3-ethyl-4-phenylthiazol-2(3H)-ylideneamino)benzoic acid (2-5)

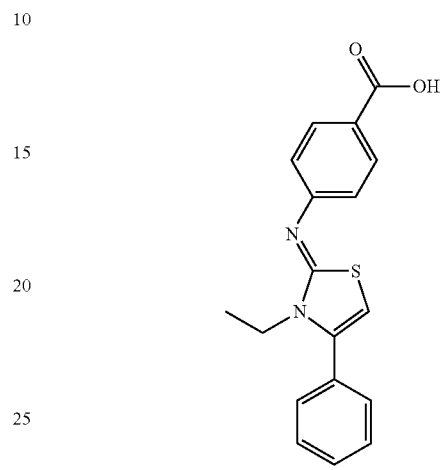

To a solution of (Z)-methyl 4-(3-ethyl-4-phenylthiazol-2(3H)-ylideneamino)benzoate (2-4) (50 mg, 0.19 mmol) in MeOH (1 mL) is added a solution of NaOH (1.0 mL of 1N aqueous solution, 1.0 mmol) and MeOH (0.5 mL). The mixture is heated at 80° C. for 1 hour and the solvent is removed. The residue is purified by preparative LC/MS to provide (Z)-4-(3-ethyl-4-phenylthiazol-2(3H)-ylideneamino)benzoic acid (2-5). HPLC-MS calculated for $C_{18}H_{16}N_2O_2S$ (M+H$^+$) 325.1. found 325.1.

Example 3

3-[3-(4-Methoxyphenyl)-1,2,4-oxadiazol-5-yl]benzoic acid

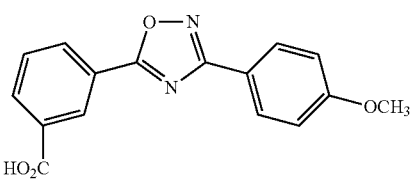 [SMILES: COc1ccc(-c2noc(-c3cccc(C(=O)O)c3)n2)cc1]

(3-[3-(4-Methoxyphenyl)-1,2,4-oxadiazol-5-yl]benzoic acid (3-4) is synthesized in two steps as shown in reaction scheme 3.

Scheme 3

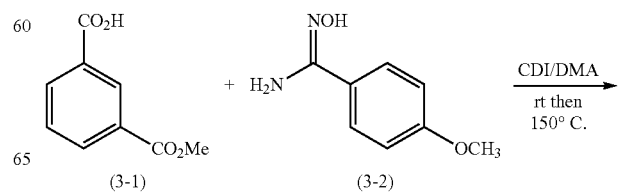

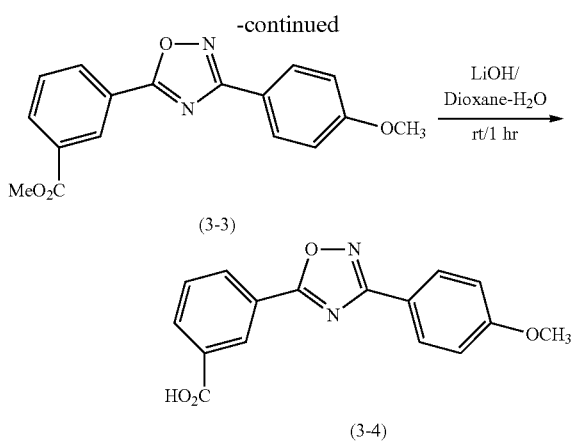

Example 3a methyl 3-[3-(4-methoxyphenyl)-1,2-4-oxadiazol-5-yl]benzoate (3-3)

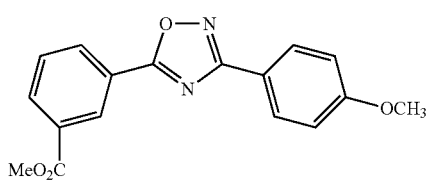 [SMILES: COC(=O)c1cccc(-c2nc(-c3ccc(OC)cc3)no2)c1]

To a solution of 3-(methoxycarbonyl)benzoic acid (3-1) (113 mg, 0.625 mmol) in N,N-dimethyl acetamide (1 mL) is added 1,1'-carbonyldiimidazole (122 mg, 0.75 mmol) at room temperature. The resulting mixture is further stirred at room temperature for 30 minutes, then N-hydroxy-4-methoxybenzimidamide (3-2) (83 mg, 0.5 mmol) is added. The reaction mixture is then stirred at room temperature for 1 hour and then at 150° C. for 4 hours. After cooled to room temperature, the resulting mixture is dissolved in ethyl acetate (50 mL), washed with water (10 mL) and brine (10 mL), dried over Na$_2$SO$_4$, filtered and evaporated. The residue is purified on silica gel (0-50% ethyl acetate in hexane) to give methyl 3-[3-(4-methoxyphenyl)-1,2-4-oxadiazol-5-yl]benzoate (3-3) as a white solid.

Example 3b

3-[3-(4-Methoxyphenyl)-1,2,4-oxadiazol-5-yl]benzoic acid (3-4)

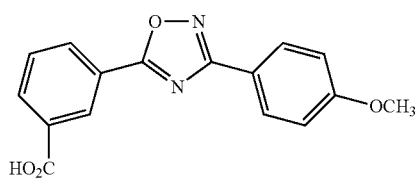 [SMILES: COc1ccc(-c2noc(-c3cccc(C(=O)O)c3)n2)cc1]

A mixture of methyl 3-[3-(4-methoxyphenyl)-1,2-4-oxadiazol-5-yl]benzoate (3-3) (30 mg, 0.097 mmol), LiOH (46 mg, 20 eq), dioxane (1 mL) and water (1 mL) is stirred at room temperature for 1 hour, then 2 mL of 1M HCl is added and a white solid then precipitates. The precipitate is filtered, washed with water and dried to give 3-[3-(4-Methoxyphenyl)-1,2,4-oxadiazol-5-yl]benzoic acid as a white solid. $^1$H NMR (DMSO-d$_6$) δ (ppm) 8.67 (dd, J=1.6, 1.6 Hz, 1H), 8.41 (ddd, J=8.4, 1.6, 1.2 Hz, 1H), 8.26 (ddd, J=8.0, 1.6, 1.2 Hz, 1H), 8.06 (dm, J=8.8 Hz, 2H), 7.81 (dd, J=8.0, 7.6 Hz, 1H), 7.15 (dm, J=8.8 Hz, 2H), 3.86 (s, 3H). HPLC-MS calculated for C$_{16}$H$_{12}$N$_2$O$_4$ (M+H$^+$) 297.08. found 297.00.

Example 4

3-[3-(4-Ethylphenyl)-1H-1,2,3-triazol-1-yl]benzoic acid

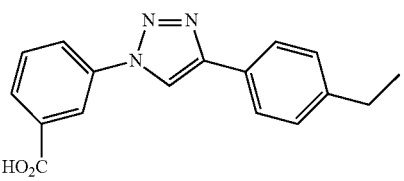 [SMILES: CCc1ccc(-c2cn(-c3cccc(C(=O)O)c3)nn2)cc1]

3-[3-(4-Ethylphenyl)-1H-1,2,3-triazol-1-yl]benzoic acid (4-4) is synthesized in two steps as shown in reaction scheme 4.

Scheme 4

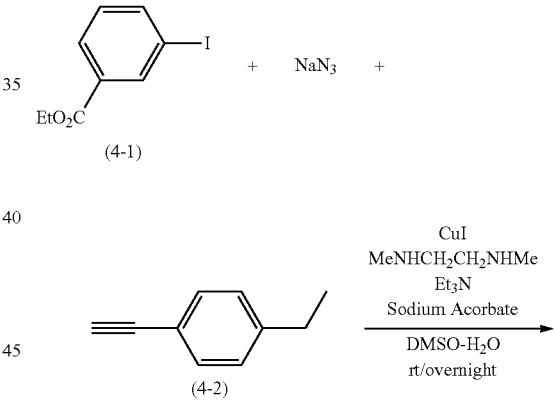

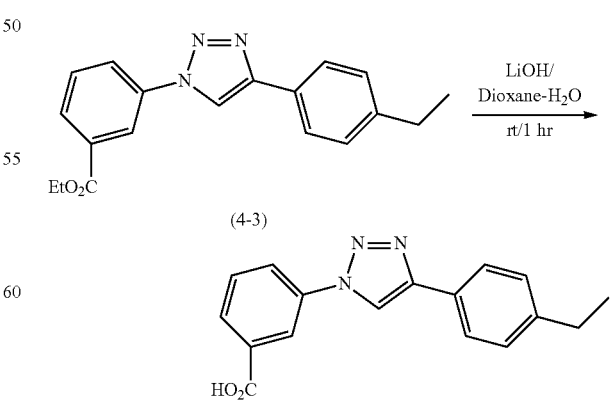

Example 4a ethyl 3-[4-(4-ethylphenyl)-1H-1,2,3-triazol-1-yl]
benzoate (4-3)

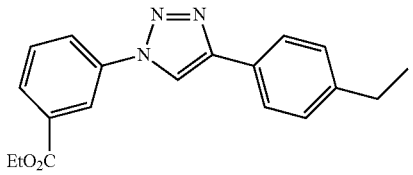 [SMILES: CCOC(=O)c1cccc(-n2cc(-c3ccc(CC)cc3)nn2)c1]

A mixture of ethyl 3-iodobenzoate (4-1) (138 mg, 0.5 mmol), sodium azide (34 mg, 0.52 mmol), 1-ethyl-4-ethynylbenzene (4-2) (65 mg, 0.5 mmol), CuI (10 mg), MeNHCH$_2$CH$_2$NHMe (11 µL), sodium ascorbate (10 mg), DMSO-H$_2$O (v/v 5:1, 1.5 mL) is stirred at room temperature for 2 hours. The reaction mixture is then poured into ethyl acetate (50 mL), washed with water (10 mL) and brine (10 mL), dried over Na$_2$SO$_4$, filtered and evaporated. The residue is purified on silica gel (0-33% ethyl acetate in hexane) to give ethyl 3-[4-(4-ethylphenyl)-1H-1,2,3-triazol-1-yl]benzoate as a white solid.

Example 4b

3-[3-(4-Ethylphenyl)-1H-1,2,3-triazol-1-yl]benzoic
acid (4-4)

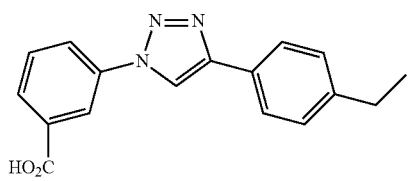 [SMILES: CCc1ccc(-c2cn(-c3cccc(C(=O)O)c3)nn2)cc1]

A mixture of ethyl 3-[4-(4-ethylphenyl)-1H-1,2,3-triazol-1-yl]benzoate (4-3) (25 mg, 0.078 mmol), LiOH (38 mg, 20 eq), dioxane (1 mL) and water (1 mL) is stirred at room temperature for 1 hour, followed by the addition of 2 mL of 1M HCl and the formation of a white solid precipitate. The precipitate is filtered, washed with water and dried to give 3-[3-(4-Ethylphenyl)-1H-1,2,3-triazol-1-yl]benzoic acid (4-4) as a white solid. $^1$H NMR (DMSO-d$_6$) δ (ppm) 9.43 (s, 1H), 8.48 (dd, J=2.0, 1.6 Hz, 1H), 8.23 (ddd, J=8.0, 2.4, 0.8 Hz, 1H), 8.06 (ddd, J=8.0, 1.6, 1.2 Hz, 1H), 7.88 (dm, J=8.4 Hz, 2H), 7.77 (dd, J=8.0, 7.6 Hz, 1H), 7.35 (dm, J=8.4 Hz, 2H), 2.66 (q, J=7.6 Hz, 2H), 1.22 (t, J=7.6 Hz, 3H). HPLC-MS calculated for C$_{17}$H$_{15}$N$_3$O$_2$ (M+H$^+$) 294.12. found 294.10.

Example 5

3-[1(4-isopropylphenyl)-1H-1,2,3-triazol-4-yl]benzoic acid

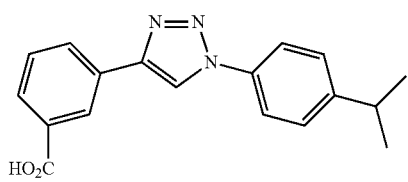 [SMILES: CC(C)c1ccc(-n2cc(-c3cccc(C(=O)O)c3)nn2)cc1]

3-[1-(4-isopropylphenyl)-1H-1,2,3-triazol-4-yl]benzoic acid (5-3) is synthesized as shown in reaction scheme 5.

Scheme 5

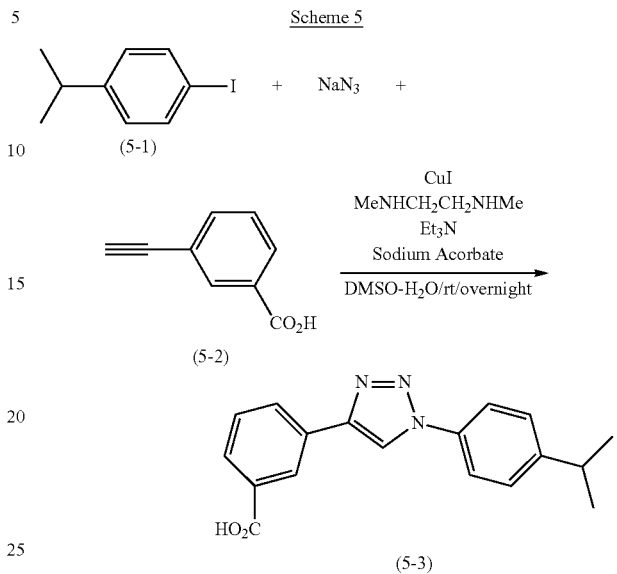

Example 5a

3-[1-(4-isopropylphenyl)-1H-1,2,3-triazol-4-yl]benzoic acid (5-3)

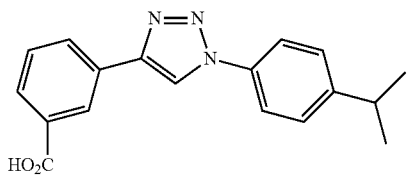 [SMILES: CC(C)c1ccc(-n2cc(-c3cccc(C(=O)O)c3)nn2)cc1]

A mixture of 1-iodo-4-isopropylbenzene (5-1) (123 mg, 0.5 mmol), sodium azide (34 mg, 0.52 mmol), 3-ethynylbenzoic acid (5-2) (73 mg, 0.5 mmol), CuI (10 mg), MeNHCH$_2$CH$_2$NHMe (11 µL), Et$_3$N (51 mg, 0.5 mmol), sodium ascorbate (10 mg), DMSO-H$_2$O (v/v 5:1, 1.5 mL) is stirred at room temperature for 2 hours followed by the addition of 2 mL of 1M HCl. The resulting mixture is poured into ethyl acetate (100 mL), washed with water (10 mL) and brine (10 mL), dried over Na$_2$SO$_4$, filtered and evaporated. The residue is purified on silica gel (0-100% ethyl acetate in hexane) to give 3-[1-(4-isopropylphenyl)-1H-1,2,3-triazol-4-yl]benzoic acid (5-3) as a white solid. $^1$H NMR (DMSO-d$_6$) δ (ppm) 9.42 (s, 1H), 8.53 (dd, J=1.6, 1.6 Hz, 1H), 8.20 (ddd, J=8.0, 1.6, 1.2 Hz, 1H), 7.95 (ddd, J=8.0, 1.6, 1.2 Hz, 1H), 7.89 (dm, J=8.8 Hz, 2H), 7.64 (dd, J=8.4, 8.0 Hz, 1H), 7.51 (dm, J=8.8 Hz, 2H), 3.00 (septet, J=6.8 Hz, 1H), 1.26 (d, J=6.8 Hz, 6H). HPLC-MS calculated for C$_{18}$H$_{17}$N$_3$O$_2$ (M+H$^+$) 308.13. found 308.10.

By repeating the procedures described in the above examples, using appropriate starting materials, the following compounds of Formula (I), as identified in Table 1, are obtained.

TABLE 1

| Compound Number | Structure | Physical Data ¹H NMR 400 MHz (CDCl₃) and/or MS (m/z) | EC$_{50}$ Range |
|---|---|---|---|
| 1 | 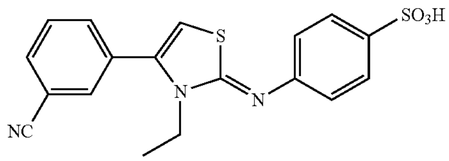 [SMILES: CCn1c(-c2cccc(C#N)c2)cs/c1=N\c1ccc(S(=O)(=O)O)cc1] | HPLC-MS calculated for $C_{18}H_{15}N_3O_3S_2$ (M + H⁺) 386.1, found 386.1. | ++++ |
| 2 | 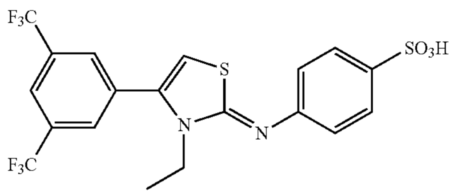 [SMILES: CCn1c(-c2cc(C(F)(F)F)cc(C(F)(F)F)c2)cs/c1=N\c1ccc(S(=O)(=O)O)cc1] | HPLC-MS calculated for $C_{19}H_{14}F_6N_2O_3S_2$ (M + H⁺) 497.0, found 497.0. | +++ |
| 3 | 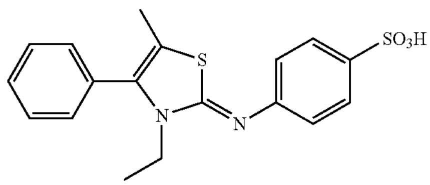 [SMILES: CCn1c(-c2ccccc2)c(C)s/c1=N\c1ccc(S(=O)(=O)O)cc1] | HPLC-MS calculated for $C_{18}H_{18}N_2O_3S_2$ (M + H⁺) 375.1, found 375.1. | ++++ |
| 4 | 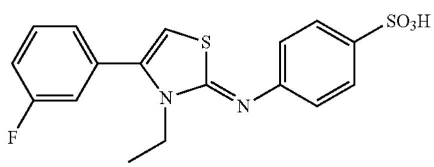 [SMILES: CCn1c(-c2cccc(F)c2)cs/c1=N\c1ccc(S(=O)(=O)O)cc1] | HPLC-MS calculated for $C_{17}H_{15}FN_2O_3S_2$ (M + H⁺) 379.1, found 379.1. | +++ |
| 5 | 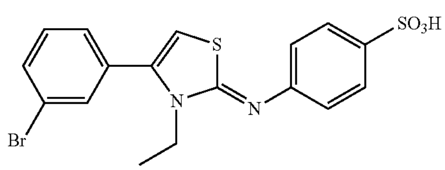 [SMILES: CCn1c(-c2cccc(Br)c2)cs/c1=N\c1ccc(S(=O)(=O)O)cc1] | HPLC-MS calculated for $C_{17}H_{15}BrN_2O_3S_2$ (M + H⁺) 439.0, found 439.0. | ++ |
| 6 | 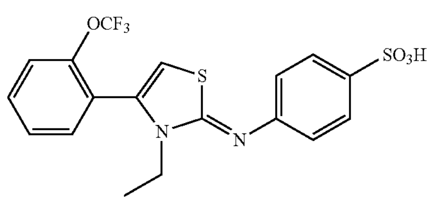 [SMILES: CCn1c(-c2ccccc2OC(F)(F)F)cs/c1=N\c1ccc(S(=O)(=O)O)cc1] | HPLC-MS calculated for $C_{18}H_{15}F_3N_2O_4S_2$ (M + H⁺) 445.0, found 445.0. | ++++ |
| 7 | 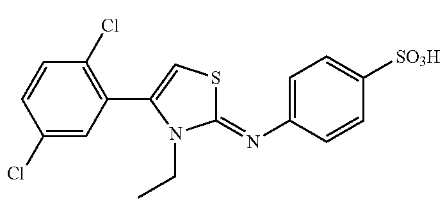 [SMILES: CCn1c(-c2cc(Cl)ccc2Cl)cs/c1=N\c1ccc(S(=O)(=O)O)cc1] | HPLC-MS calculated for $C_{17}H_{14}Cl_2N_2O_3S_2$ (M + H⁺) 429.0, found 429.0. | ++ |
| 8 | 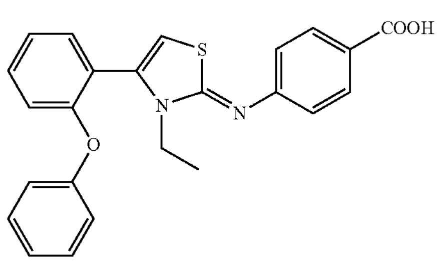 [SMILES: CCn1c(-c2ccccc2Oc2ccccc2)cs/c1=N\c1ccc(C(=O)O)cc1] | HPLC-MS calculated for $C_{24}H_{20}N_2O_3S$ (M + H⁺) 417.1, found 417.1. | ++++ |

TABLE 1-continued

| Compound Number | Structure | Physical Data <br> $^1$H NMR 400 MHz (CDCl$_3$) and/or MS (m/z) | EC$_{50}$ Range |
|---|---|---|---|
| 9 | 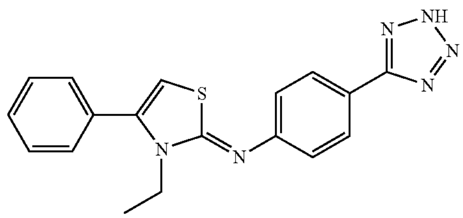 [SMILES: CCn1c(-c2ccccc2)cs/c1=N\c1ccc(-c2nn[nH]n2)cc1] | HPLC-MS calculated for C$_{18}$H$_{16}$N$_6$S (M + H$^+$) 349.1, found 349.1. | ++ |
| 10 | 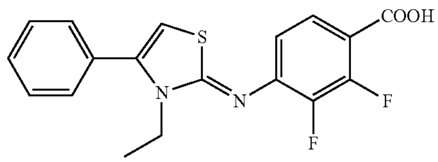 | HPLC-MS calculated for C$_{18}$H$_{14}$F$_2$N$_2$O$_2$S (M + H$^+$) 361.1, found 361.1. | +++ |
| 11 | 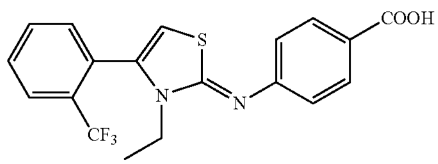 [SMILES: CCn1c(-c2ccccc2C(F)(F)F)cs/c1=N\c1ccc(C(=O)O)cc1] | HPLC-MS calculated for C$_{19}$H$_{15}$F$_3$N$_2$O$_2$S (M + H$^+$) 393.1, found 393.1. | ++ |
| 12 | 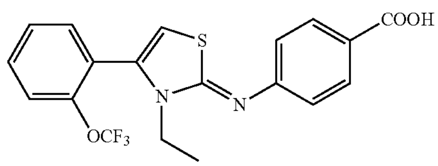 [SMILES: CCn1c(-c2ccccc2OC(F)(F)F)cs/c1=N\c1ccc(C(=O)O)cc1] | HPLC-MS calculated for C$_{19}$H$_{15}$F$_3$N$_2$O$_3$S (M + H$^+$) 409.1, found 409.1. | +++ |
| 13 | 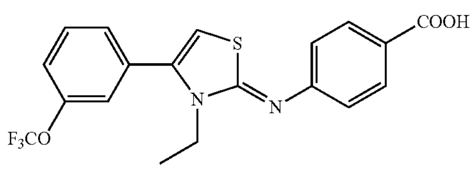 [SMILES: CCn1c(-c2cccc(OC(F)(F)F)c2)cs/c1=N\c1ccc(C(=O)O)cc1] | HPLC-MS calculated for C$_{19}$H$_{15}$F$_3$N$_2$O$_3$S (M + H$^+$) 409.1, found 409.1. | ++++ |
| 14 | 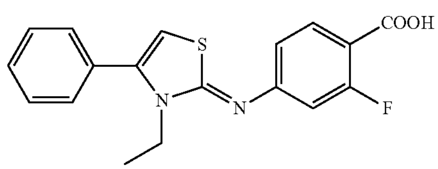 | HPLC-MS calculated for C$_{18}$H$_{15}$FN$_2$O$_2$S (M + H$^+$) 343.1, found 343.1. | ++ |
| 15 | 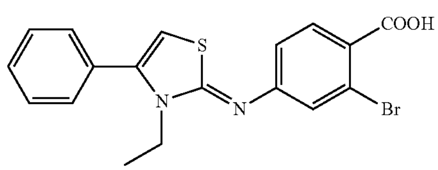 [SMILES: CCn1c(-c2ccccc2)cs/c1=N\c1ccc(C(=O)O)c(Br)c1] | $^1$H NMR (CD$_3$OD, 400 MHz) δ 7.97 (d, J = 8.0 Hz, 1H), 7.71 (d, J = 2.0 Hz, 1H), 7.58-7.50 (m, 5H), 7.43 (dd, J = 8.0, 2.0 Hz, 1H), 6.64 (s, 1H), 4.04 (q, J = 7.2 Hz, 2H), 1.25 (t, J = 7.2 Hz, 3H); HPLC-MS calculated for C$_{18}$H$_{15}$BrN$_2$O$_2$S (M + H$^+$) 403.0, found 403.0. | ++ |
| 16 | 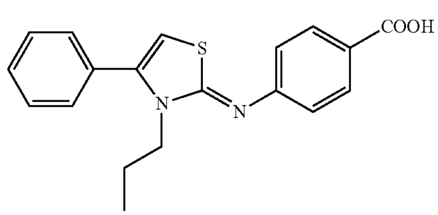 [SMILES: CCCn1c(-c2ccccc2)cs/c1=N\c1ccc(C(=O)O)cc1] | HPLC-MS calculated for C$_{19}$H$_{18}$N$_2$O$_2$S (M + H$^+$) 339.1, found 339.1. | +++ |

TABLE 1-continued

| Compound Number | Structure | Physical Data<br>¹H NMR 400 MHz<br>(CDCl₃)<br>and/or MS (m/z) | EC₅₀ Range |
|---|---|---|---|
| 17 | 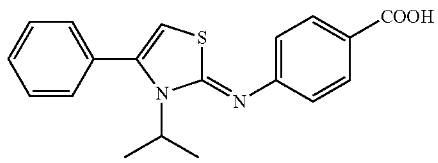 [SMILES: CC(C)n1c(-c2ccccc2)cs/c1=N\c1ccc(C(=O)O)cc1] | HPLC-MS calculated for $C_{19}H_{18}N_2O_2S$ (M + H⁺) 339.1, found 339.1. | ++ |
| 18 | 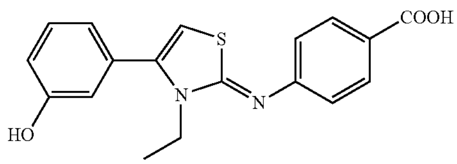 [SMILES: CCn1c(-c2cccc(O)c2)cs/c1=N\c1ccc(C(=O)O)cc1] | HPLC-MS calculated for $C_{18}H_{16}N_2O_3S$ (M + H⁺) 341.1, found 341.1. | +++ |
| 19 | 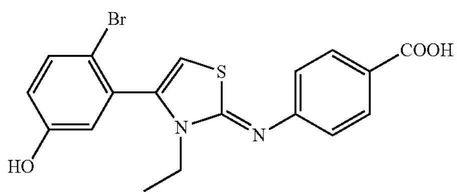 [SMILES: CCn1c(-c2cc(O)ccc2Br)cs/c1=N\c1ccc(C(=O)O)cc1] | ¹H NMR (CD₃OD, 400 MHz) δ 8.19 (d, J = 8.8 Hz, 2H), 7.60 (m, 3H), 6.98 (m, 2H), 6.92 (s, 1H), 4.15 (m, 1H), 3.91 (m, 1H), 1.31 (t, J = 7.2 Hz, 3H); HPLC-MS calculated for $C_{18}H_{15}BrN_2O_3S$ (M + H⁺) 419.0, found 419.0. | ++++ |
| 20 | 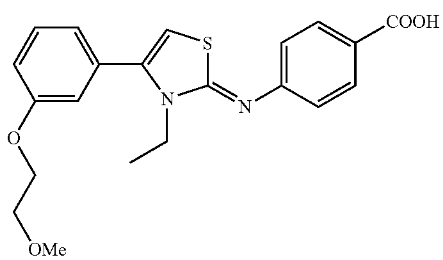 [SMILES: CCn1c(-c2cccc(OCCOC)c2)cs/c1=N\c1ccc(C(=O)O)cc1] | HPLC-MS calculated for $C_{21}H_{22}N_2O_4S$ (M + H⁺) 399.1, found 399.1. | ++ |
| 21 | 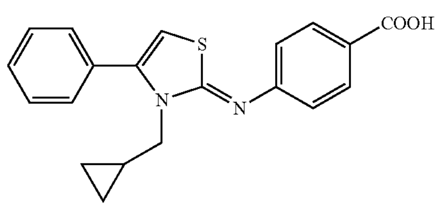 [SMILES: O=C(O)c1ccc(/N=c2\scc(-c3ccccc3)n2CC2CC2)cc1] | HPLC-MS calculated for $C_{20}H_{18}N_2O_2S$ (M + H⁺) 351.1, found 351.1. | +++ |
| 22 | 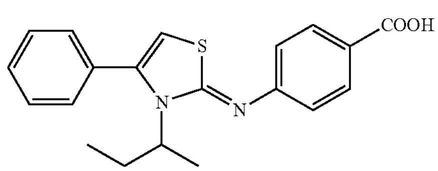 [SMILES: CCC(C)n1c(-c2ccccc2)cs/c1=N\c1ccc(C(=O)O)cc1] | HPLC-MS calculated for $C_{20}H_{20}N_2O_2S$ (M + H⁺) 353.1, found 353.1. | ++++ |
| 23 | 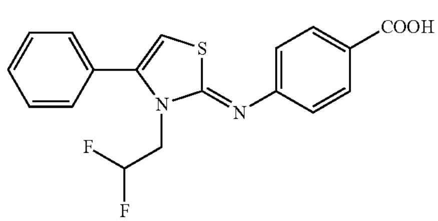 [SMILES: O=C(O)c1ccc(/N=c2\scc(-c3ccccc3)n2CC(F)F)cc1] | HPLC-MS calculated for $C_{18}H_{14}F_2N_2O_2S$ (M + H⁺) 361.1, found 361.1. | ++ |

TABLE 1-continued

| Compound Number | Structure | Physical Data ¹H NMR 400 MHz (CDCl₃) and/or MS (m/z) | EC$_{50}$ Range |
|---|---|---|---|
| 24 | 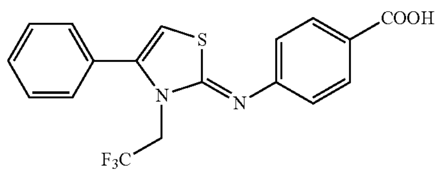 [SMILES: O=C(O)c1ccc(/N=c2\scc(-c3ccccc3)n2CC(F)(F)F)cc1] | HPLC-MS calculated for $C_{18}H_{13}F_3N_2O_2S$ (M + H⁺) 379.1, found 379.1. | ++ |
| 25 | 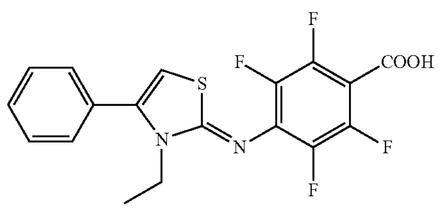 [SMILES: CCn1c(-c2ccccc2)cs/c1=N\c1c(F)c(F)c(C(=O)O)c(F)c1F] | HPLC-MS calculated for $C_{18}H_{12}F_4N_2O_2S$ (M + H⁺) 397.1, found 397.1. | +++ |
| 26 | 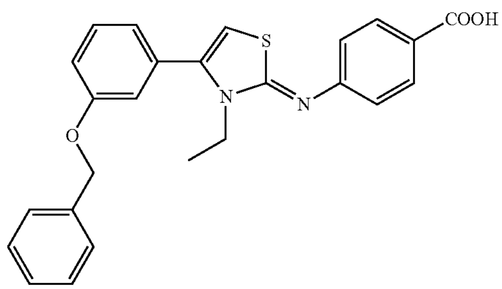 [SMILES: CCn1c(-c2cccc(OCc3ccccc3)c2)cs/c1=N\c1ccc(C(=O)O)cc1] | HPLC-MS calculated for $C_{25}H_{22}N_2O_3S$ (M + H⁺) 431.1, found 431.1. | ++++ |
| 27 | 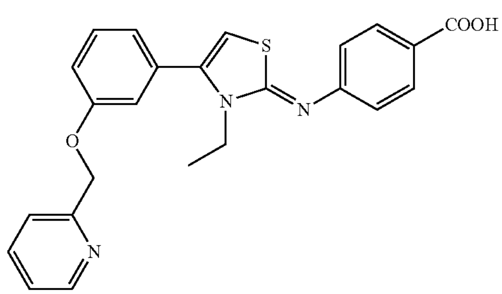 [SMILES: CCn1c(-c2cccc(OCc3ccccn3)c2)cs/c1=N\c1ccc(C(=O)O)cc1] | HPLC-MS calculated for $C_{24}H_{21}N_3O_3S$ (M + H⁺) 432.1, found 432.1. | ++++ |
| 28 | 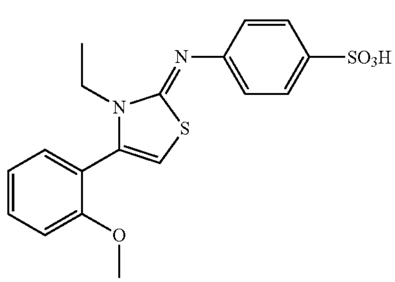 [SMILES: CCn1c(-c2ccccc2OC)cs/c1=N\c1ccc(S(=O)(=O)O)cc1] | HPLC-MS calculated for $C_{18}H_{18}N_2O_4S_2$ (M + H⁺) 391.1, found 391.1. | ++ |

TABLE 1-continued

| Compound Number | Structure | Physical Data<br>¹H NMR 400 MHz<br>(CDCl₃)<br>and/or MS (m/z) | EC₅₀ Range |
|---|---|---|---|
| 29 | 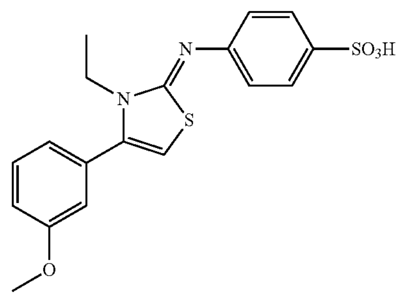 [SMILES: CCn1c(-c2cccc(OC)c2)cs/c1=N\c1ccc(S(=O)(=O)O)cc1] | HPLC-MS calculated for $C_{18}H_{18}N_2O_4S_2$ (M + H⁺) 391.1, found 391.1. | +++ |
| 30 | 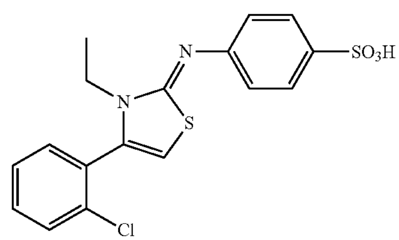 [SMILES: CCn1c(-c2ccccc2Cl)cs/c1=N\c1ccc(S(=O)(=O)O)cc1] | HPLC-MS calculated for $C_{17}H_{15}ClN_2O_3S_2$ (M + H⁺) 395.0, found 395.0. | ++ |
| 31 | 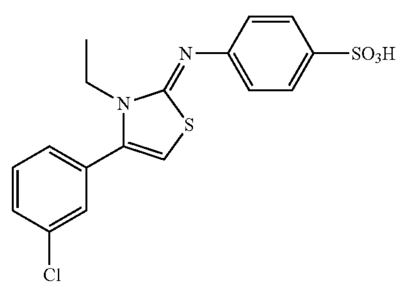 [SMILES: CCn1c(-c2cccc(Cl)c2)cs/c1=N\c1ccc(S(=O)(=O)O)cc1] | HPLC-MS calculated for $C_{17}H_{15}ClN_2O_3S_2$ (M + H⁺) 395.0, found 395.0. | + |
| 32 | 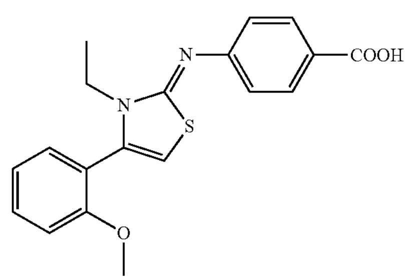 [SMILES: CCn1c(-c2ccccc2OC)cs/c1=N\c1ccc(C(=O)O)cc1] | HPLC-MS calculated for $C_{19}H_{18}N_2O_3S$ (M + H⁺) 355.1, found 355.1. | ++++ |
| 33 | 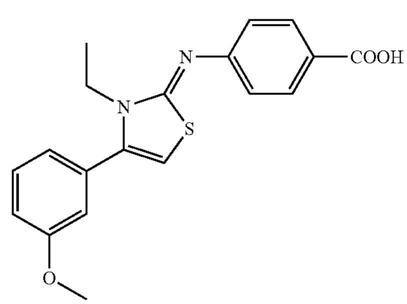 [SMILES: CCn1c(-c2cccc(OC)c2)cs/c1=N\c1ccc(C(=O)O)cc1] | HPLC-MS calculated for $C_{19}H_{18}N_2O_3S$ (M + H⁺) 355.1, found 355.1. | ++++ |

TABLE 1-continued

| Compound Number | Structure | Physical Data $^1$H NMR 400 MHz (CDCl$_3$) and/or MS (m/z) | EC$_{50}$ Range |
|---|---|---|---|
| 34 | (3-ethyl-4-(2-chlorophenyl)thiazol-2-ylidene)amino-benzoic acid structure | HPLC-MS calculated for C$_{18}$H$_{15}$ClN$_2$O$_2$S (M + H$^+$) 359.1, found 359.1. | ++ |
| 35 | (3-ethyl-4-(3-chlorophenyl)thiazol-2-ylidene)amino-benzoic acid structure | HPLC-MS calculated for C$_{18}$H$_{15}$ClN$_2$O$_2$S (M + H$^+$) 359.1, found 359.1. | ++ |
| 36 | (3-ethyl-4-phenylthiazol-2-ylidene)amino-benzoic acid structure | HPLC-MS calculated for C$_{18}$H$_{16}$N$_2$O$_2$S (M + H$^+$) 325.1, found 325.1. | +++ |
| 37 | (3-ethyl-4-phenylthiazol-2-ylidene)amino-benzenesulfonic acid structure | $^1$H NMR (CD$_3$OD, 400 MHz) δ 8.01 (d, J = 8.0 Hz, 2H), 7.49-7.61 (m, 7H), 6.92 (s, 1H), 4.14 (q, J = 7.2 Hz, 2H), 1.32 (t, J = 7.2 Hz, 3H); HPLC-MS calculated for C$_{17}$H$_{16}$BrN$_2$O$_3$S$_2$ (M + H$^+$) 361.1, found 361.1. | ++ |
| 38 | (3-ethyl-4-(2,6-dichlorophenyl)thiazol-2-ylidene)amino-benzoic acid structure | HPLC-MS calculated for C$_{18}$H$_{14}$Cl$_2$N$_2$O$_2$S (M + H$^+$) 393.0, found 3393.0. | ++ |

TABLE 1-continued

| Compound Number | Structure | Physical Data $^1$H NMR 400 MHz (CDCl$_3$) and/or MS (m/z) | EC$_{50}$ Range |
|---|---|---|---|
| 39 | 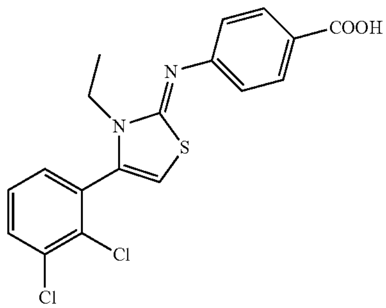 [SMILES: CCn1c(-c2cccc(Cl)c2Cl)cs/c1=N\c1ccc(C(=O)O)cc1] | HPLC-MS calculated for C$_{18}$H$_{14}$Cl$_2$N$_2$O$_2$S (M + H$^+$) 393.0, found 393.0. | ++ |
| 40 | 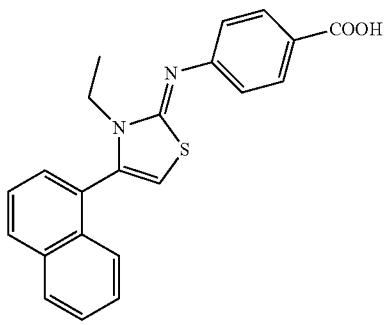 [SMILES: CCn1c(-c2cccc3ccccc23)cs/c1=N\c1ccc(C(=O)O)cc1] | HPLC-MS calculated for C$_{22}$H$_{18}$N$_2$O$_2$S (M + H$^+$) 375.1, found 375.1. | +++ |
| 41 | 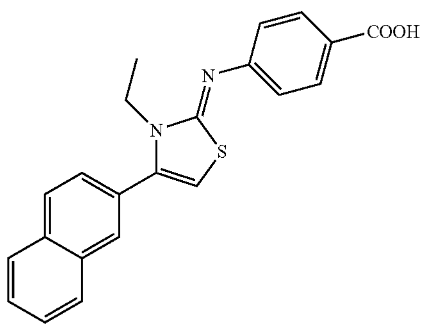 [SMILES: CCn1c(-c2ccc3ccccc3c2)cs/c1=N\c1ccc(C(=O)O)cc1] | HPLC-MS calculated for C$_{22}$H$_{18}$N$_2$O$_2$S (M + H$^+$) 375.1, found 375.1. | +++ |
| 42 | 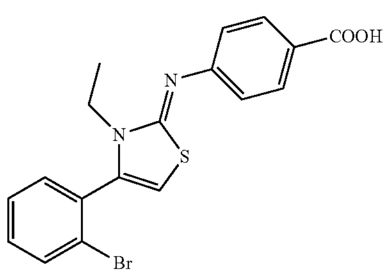 [SMILES: CCn1c(-c2ccccc2Br)cs/c1=N\c1ccc(C(=O)O)cc1] | HPLC-MS calculated for C$_{18}$H$_{15}$BrN$_2$O$_2$S (M + H$^+$) 403.0, found 403.0. | + |
| 43 | 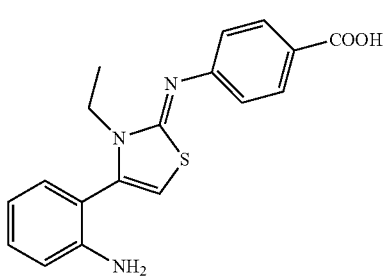 | HPLC-MS calculated for C$_{18}$H$_{17}$N$_3$O$_2$S (M + H$^+$) 340.1, found 340.1. | + |

TABLE 1-continued

| Compound Number | Structure | Physical Data $^1$H NMR 400 MHz (CDCl$_3$) and/or MS (m/z) | EC$_{50}$ Range |
|---|---|---|---|
| 44 | 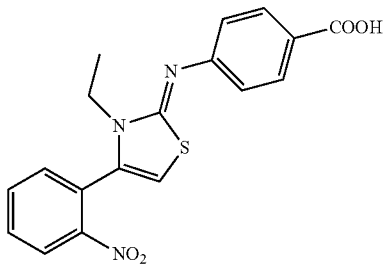 | HPLC-MS calculated for C$_{18}$H$_{15}$N$_3$O$_4$S (M + H$^+$) 370.1, found 370.1. | ++++ |
| 45 | 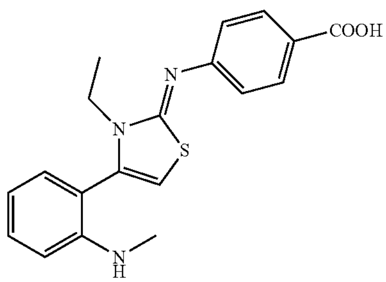 [SMILES: CCn1c(-c2ccccc2NC)cs/c1=N\c1ccc(C(=O)O)cc1] | $^1$H NMR (CD$_3$OD, 400 MHz) δ 8.19 (d, J = 8.8 Hz, 2H), 7.60 (d, J = 8.4 Hz, 2H), 7.43 (td, J = 8.0, 1.6 Hz, 1H), 7.17 (dd, J = 8.0, 1.6 Hz, 1H), 6.84 (s, 1H), 6.78 (d, J = 7.6 Hz, 1H), 6.77 (t, J = 7.2 Hz, 1H), 4.05 (m, 1H), 3.88 (m, 1H), 2.82 (s, 3H), 1.25 (t, J = 7.2 Hz, 3H); HPLC-MS calculated for C$_{19}$H$_{19}$N$_3$O$_2$S (M + H$^+$) 354.1, found 354.1. | ++++ |
| 46 | 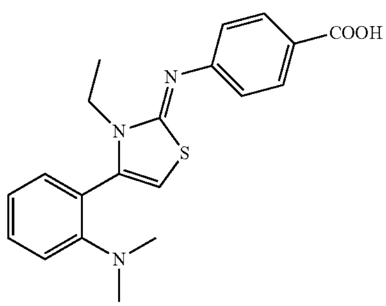 [SMILES: CCn1c(-c2ccccc2N(C)C)cs/c1=N\c1ccc(C(=O)O)cc1] | $^1$H NMR (CD$_3$OD, 400 MHz) δ 8.22 (d, J = 8.8 Hz, 2H), 7.69 (d, J = 8.8 Hz, 2H), 7.583 (td, J = 8.0, 1.6 Hz, 1H), 7.38 (dd, J = 8.0, 1.6 Hz, 1H), 7.33 (d, J = 8.4 Hz, 1H), 7.20 (t, J = 8.0 Hz, 1H), 7.09 (s, 1H), 4.09 (br, 2H), 2.73 (s, 6H), 1.23 (t, J = 7.2 Hz, 3H); HPLC-MS calculated for C$_{10}$H$_{21}$N$_3$O$_2$S (M + H$^+$) 368.1, found 368.1. | ++++ |
| 47 | 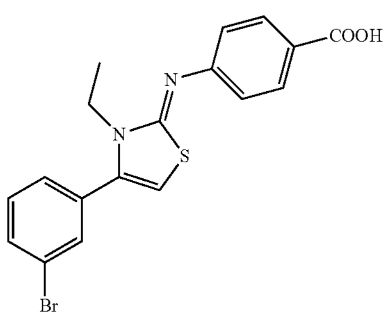 [SMILES: CCn1c(-c2cccc(Br)c2)cs/c1=N\c1ccc(C(=O)O)cc1] | HPLC-MS calculated for C$_{18}$H$_{15}$BrN$_2$O$_2$S (M + H$^+$) 403.0, found 403.0. | ++ |
| 48 | 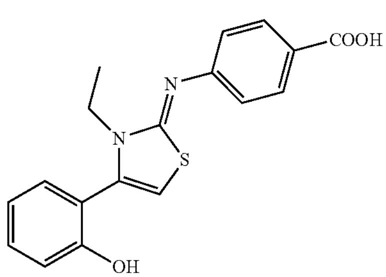 [SMILES: CCn1c(-c2ccccc2O)cs/c1=N\c1ccc(C(=O)O)cc1] | HPLC-MS calculated for C$_{18}$H$_{16}$N$_2$O$_3$S (M + H$^+$) 341.1, found 341.1. | ++ |

TABLE 1-continued

| Compound Number | Structure | Physical Data <br> ¹H NMR 400 MHz (CDCl₃) and/or MS (m/z) | EC₅₀ Range |
|---|---|---|---|
| 49 | (structure: 4-[(3-ethyl-4-(3-cyanophenyl)thiazol-2(3H)-ylidene)amino]benzoic acid) | HPLC-MS calculated for C₁₉H₁₅N₃O₂S (M + H⁺) 350.1, found 350.1. | +++ |
| 50 | (structure: 4-[(3-ethyl-4-(5-bromo-2-hydroxyphenyl)thiazol-2(3H)-ylidene)amino]benzoic acid) | HPLC-MS calculated for C₁₈H₁₅BrN₂O₃S (M + H⁺) 419.0, found 419.0. | ++ |
| 51 | (structure: 3-[3-(4-methoxyphenyl)-1,2,4-oxadiazol-5-yl]benzoic acid) | ¹H NMR (DMSO-d₆) δ (ppm) 8.67 (dd, J = 1.6, 1.6 Hz, 1H), 8.41 (ddd, J = 8.4, 1.6, 1.2 Hz, 1H), 8.26 (ddd, J = 8.0, 1.6, 1.2 Hz, 1H), 8.06 (dm, J = 8.8 Hz, 2H), 7.81 (dd, J = 8.0, 7.6 Hz, 1H), 7.15 (dm, J = 8.8 Hz, 2H), 3.86 (s, 3H). HPLC-MS calculated for C₁₆H₁₂N₂O₄ (M + H⁺) 297.08, found 297.00. | ++ |
| 52 | (structure: 4-[3-(4-methoxyphenyl)-1,2,4-oxadiazol-5-yl]benzoic acid) | HPLC-MS calculated for C₁₆H₁₂N₂O₄ (M + H⁺) 297.08, found 297.10. | +++++ |
| 53 | (structure: 3-[3-(3-methoxyphenyl)-1,2,4-oxadiazol-5-yl]benzoic acid) | HPLC-MS calculated for C₁₆H₁₂N₂O₄ (M + H⁺) 297.08, found 297.10. | ++++ |
| 54 | (structure: 3-[1-(4-methoxyphenyl)-1H-1,2,3-triazol-4-yl]benzoic acid) | ¹H NMR (DMSO-d₆) δ (ppm) 9.36 (s, 1H), 8.52 (m, 1H), 8.18 (dm, J = 8.0 Hz, 1H), 7.94 (dm, 8.0 Hz, 1H), 7.89 (dm, J = 9.2 Hz, 2H), 7.63 (dd, J = 8.0, 7.6 Hz, 1H), 7.18 (dm, J = 9.2 Hz, 2H), 3.85 (s, 3H). HPLC-MS calculated for C₁₆H₁₃N₃O₃ (M + H⁺) 296.10, found 295.80. | +++++ |

TABLE 1-continued

| Compound Number | Structure | Physical Data <br> ¹H NMR 400 MHz <br> (CDCl₃) <br> and/or MS (m/z) | EC₅₀ Range |
|---|---|---|---|
| 55 | 3-(1-(3-carboxyphenyl)-1H-1,2,3-triazol-4-yl), 4-methoxyphenyl structure with HO₂C group | ¹H NMR (DMSO-d₆) δ (ppm) 9.36 (s, 1H), 8.47 (dd, J = 1.6, 1.2 Hz, 1H), 8.22 (ddd, J = 8.0, 2.4, 0.8 Hz, 1H), 8.05 (ddd, J = 7.6, 1.2, 1.2 Hz, 1H), 7.90 (dm, J = 8.8 Hz, 2H), 7.77 (dd, J = 8.0, 8.0 Hz, 1H), 7.07 (dm, J = 8.8 Hz, 2H), 3.81 (s, 3H). HPLC-MS calculated for $C_{16}H_{13}N_3O_3$ (M + H⁺) 296.10, found 296.10. | +++++ |
| 56 | 1,2,4-oxadiazole with phenyl-HO₂C and 4-methoxyphenyl | ¹H NMR (DMSO-d₆) δ (ppm) 8.63 (m, 1H), 8.32 (dm, J = 7.6 Hz, 1H), 8.20-8.14 (m, 1H), 8.17 (dm, J = 8.8 Hz, 2H), 7.74 (dd, J = 8.0, 7.6 Hz, 1H), 7.20 (dm, J = 8.8 Hz, 2H), 3.89 (s, 3H). HPLC-MS calculated for $C_{16}H_{12}N_2O_4$ (M + H⁺) 297.08, found 297.00. | +++ |
| 57 | triazole with HO₂C-phenyl and 4-methylphenyl | ¹H NMR (DMSO-d₆) δ (ppm) 9.42 (s, 1H), 8.48 (dd, J = 2.0, 1.6 Hz, 1H), 8.23 (ddd, J = 8.0, 2.4, 1.2 Hz, 1H), 8.05 (ddd, J = 8.0, 2.4, 1.2 Hz, 1H), 7.86 (dm, J = 8.0 Hz, 2H), 7.77 (dd, J = 8.0, 7.6 Hz, 1H), 7.32 (dm, J = 8.0 Hz, 2H), 2.36 (s, 3H). HPLC-MS calculated for $C_{16}H_{13}N_3O_2$ (M + H⁺) 280.10, found 280.10. | +++++ |
| 58 | triazole with HO₂C-phenyl and 4-CF₃-phenyl | HPLC-MS calculated for $C_{16}H_{10}F_3N_3O_2$ (M + H⁺) 334.07, found 334.00. | +++++ |
| 59 | triazole with HO₂C-phenyl and 4-Cl-phenyl | ¹H NMR (DMSO-d₆) δ (ppm) 9.53 (s, 1H), 8.47 (dd, J = 2.0, 1.6 Hz, 1H), 8.23 (ddd, J = 8.0, 2.4, 0.8 Hz, 1H), 8.07 (ddd, J = 8.0, 2.4, 1.2 Hz, 1H), 7.99 (dm, J = 8.4 Hz, 2H), 7.78 (dd, J = 8.0, 8.0 Hz, 1H), 7.59 (dm, J = 8.8 Hz, 2H). HPLC-MS calculated for $C_{15}H_{10}ClN_3O_2$ (M + H⁺) 300.05, found 300.00. | +++++ |
| 60 | triazole with HO₂C-phenyl and 2-F-phenyl | HPLC-MS calculated for $C_{15}H_{10}FN_3O_2$ (M + H⁺) 284.08, found 284.10. | +++++ |

TABLE 1-continued

| Compound Number | Structure | Physical Data <br> $^1$H NMR 400 MHz (CDCl$_3$) and/or MS (m/z) | EC$_{50}$ Range |
|---|---|---|---|
| 61 | 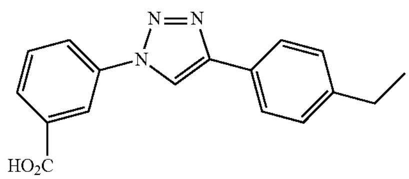 [SMILES: CCc1ccc(-c2cn(-c3cccc(C(=O)O)c3)nn2)cc1] | $^1$H NMR (DMSO-d$_6$) δ (ppm) 9.43 (s, 1H), 8.48 (dd, J = 2.0, 1.6 Hz, 1H), 8.23 (ddd, J = 8.0, 2.4, 0.8 Hz, 1H), 8.06 (ddd, J = 8.0, 1.6, 1.2 Hz, 1H), 7.88 (dm, J = 8.4 Hz, 2H), 7.77 (dd, J = 8.0, 7.6 Hz, 1H), 7.35 (dm, J = 8.4 Hz, 2H), 2.66 (q, J = 7.6 Hz, 2H), 1.22 (t, J = 7.6 Hz, 3H). HPLC-MS calculated for C$_{17}$H$_{15}$N$_3$O$_2$ (M + H$^+$) 294.12, found 294.10. | ++++ |
| 62 | 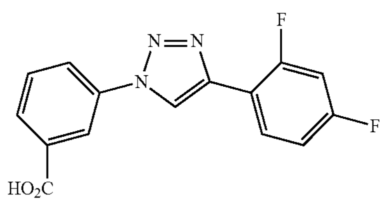 [SMILES: O=C(O)c1cccc(-n2cc(-c3ccc(F)cc3F)nn2)c1] | $^1$H NMR (DMSO-d$_6$) δ (ppm) 9.24 (d, J = 3.2 Hz, 1H), 8.51 (dd, J = 2.0, 2.0 Hz, 1H), 8.28 (ddd, J = 8.0, 2.4, 0.8 Hz, 1H), 8.22 (td, J = 8.8, 6.4 Hz, 1H), 8.07 (ddd, 8.0, 1.6, 1.2 Hz, 1H), 7.77 (dd, J = 8.4, 8.0 Hz, 1H), 7.49 (ddd, J = 10.8, 9.6, 2.8 Hz, 1H), 7.29 (tdd, J = 8.4, 2.8, 0.8 Hz, 1H). HPLC-MS calculated for C$_{15}$H$_9$F$_2$N$_3$O$_2$ (M + H$^+$) 302.07, found 302.00. | +++ |
| 63 | 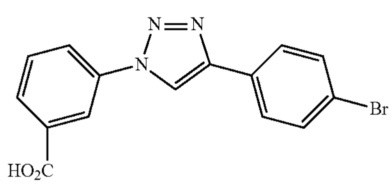 [SMILES: O=C(O)c1cccc(-n2cc(-c3ccc(Br)cc3)nn2)c1] | HPLC-MS calculated for C$_{15}$H$_{10}$BrN$_3$O$_2$ (M + H$^+$) 344.00, found 344.00. | +++++ |
| 64 | 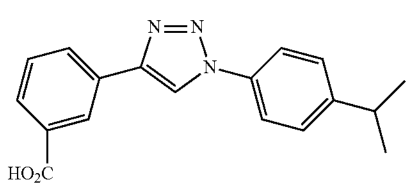 [SMILES: CC(C)c1ccc(-n2cc(-c3cccc(C(=O)O)c3)nn2)cc1] | $^1$H NMR (DMSO-d$_6$) δ (ppm) 9.42 (s, 1H), 8.53 (dd, J = 1.6, 1.6 Hz, 1H), 8.20 (ddd, J = 8.0, 1.6, 1.2 Hz, 1H), 7.95 (ddd, J = 8.0, 1.6, 1.2 Hz, 1H), 7.89 (dm, J = 8.8 Hz, 2H), 7.64 (dd, J = 8.4, 8.0 Hz, 1H), 7.51 (dm, J = 8.8 Hz, 2H), 3.00 (septet, J = 6.8 Hz, 1H), 1.26 (d, J = 6.8 Hz, 6H). HPLC-MS calculated for C$_{18}$H$_{17}$N$_3$O$_2$ (M + H$^+$) 308.13, found 308.10. | ++++ |
| 65 | 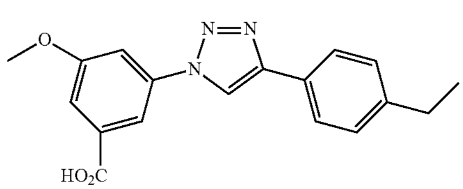 [SMILES: CCc1ccc(-c2cn(-c3cc(OC)cc(C(=O)O)c3)nn2)cc1] | $^1$H NMR (DMSO-d$_6$) δ (ppm) 9.42 (s, 1H), 8.09 (dd, J = 1.6, 1.2 Hz, 1H), 7.87 (dm, J = 8.0 Hz, 2H), 7.79 (dd, J = 2.4, 2.0 Hz, 1H), 7.54 (dd, J = 2.4, 1.2 Hz, 1H), 7.35 (dm, J = 8.4 Hz, 2H), 3.94 (s, 3H), 2.65 (q, J = 7.6 Hz, 2H), 1.22 (t, J = 7.6 Hz, 3H). HPLC-MS calculated for C$_{18}$H$_{17}$N$_3$O$_3$ (M + H$^+$) 324.13, found 324.10. | +++++ |

TABLE 1-continued

| Compound Number | Structure | Physical Data $^1$H NMR 400 MHz (CDCl$_3$) and/or MS (m/z) | EC$_{50}$ Range |
|---|---|---|---|
| 66 | F-phenyl-triazole-phenyl-ethyl with HO$_2$C | HPLC-MS calculated for C$_{17}$H$_{14}$FN$_3$O$_2$ (M + H$^+$) 312.11, found 312.10. | ++++ |
| 67 | phenyl-triazole-F-phenyl-methyl with HO$_2$C | $^1$H NMR (DMSO-d$_6$) δ (ppm) 9.19 (d, J = 1.6 Hz, 1H), 8.53 (dd, J = 1.6, 1.6 Hz, 1H), 8.20 (ddd, J = 8.0, 1.6, 1.2 Hz, 1H), 7.95 (ddd, J = 8.0, 1.6, 1.2 Hz, 1H), 7.77 (dd, J = 8.4, 8.0 Hz, 1H), 7.63 (dd, J = 8.0, 7.6 Hz, 1H), 7.45 (dm, J = 12.0 Hz, 1H), 7.29 (dm, J = 8.0 Hz, 1H), 2.44 (s, 3H). HPLC-MS calculated for C$_{16}$H$_{12}$FN$_3$O$_2$ (M + H$^+$) 298.09, found 298.10. | ++ |
| 68 | Cl-phenyl-triazole-phenyl-ethyl with CO$_2$H | HPLC-MS calculated for C$_{17}$H$_{14}$FN$_3$O$_2$ (M + H$^+$) 328.71, found 328.70. | ++++++ |
| 69 | F-phenyl-triazole-phenyl-ethyl with HO$_2$C | HPLC-MS calculated for C$_{17}$H$_{14}$FN$_3$O$_2$ (M + H$^+$) 312.11, found 312.10. | +++++ |
| 70 | F-phenyl-triazole-phenyl-ethyl with HO$_2$C | $^1$H NMR (DMSO-d$_6$) δ (ppm) 9.12 (d, J = 2.0 Hz, 1H), 8.39 (dd, J = 7.2, 2.0 Hz, 1H), 8.16 (ddd, J = 8.8, 4.8, 2.0 Hz, 1H), 7.88 (dm, J = 8.4 Hz, 2H), 7.74 (dd, J = 10.4, 8.8 Hz, 1H), 7.34 (dm, J = 8.4 Hz, 2H), 2.65 (q, J = 7.6 Hz, 2H), 1.24 (t, J = 7.6 Hz, 3H). HPLC-MS calculated for C$_{17}$H$_{14}$FN$_3$O$_2$ (M + H$^+$) 312.11, found 312.00. | +++++ |

Assays

The suitability of a compound to modulate G protein-coupled receptor 120 (GPR120) are tested following the assays described below, or using methods known in the art, such as those described in EP 1688138, incorporated herein by reference for such assay methodologies.

Generation of GPR120—Expressing Cells

Human GPR120 stable cell-line was generated in HEK293 cells. GPR120 (Accession number BC101175) is fused to a promiscuous G protein, Gα16. The expression plasmid is transfected into HEK293 cells using Fugene6 following manufacturer's instruction. Stable cell-lines are generated following drug selection.

FLIPR Assay

FLIPR (Fluorimetric Imaging Plate Reader, Molecular Devices) assays are performed to measure agonist-induced calcium mobilization in the GPR120-expressing cells. One day before the FLIPR assay, HEK293-GPR120-Gα16 cells are seeded into poly-D-lysine coated black-wall-clear bottom 384 well plates (Falcon) at 25,000 cells per well in 40 μl DMEM supplemented with 1% of FBS. The cells are incubated overnight at 37° C. in a humidified incubator. The medium is aspirated on the day of the FLIPR assay. The cells are incubated with 50 μl/well of the assay buffer (HBSS, 20 mM HEPES, 2.5 mM probenecid, pH7.4) containing Fluo-4 NM dye (Invitrogen cat# F36205) at 37° C. for 45 minutes, and then equilibrated at room temperature for 30 minutes.

Compounds are dissolved in DMSO and diluted to desired concentrations with assay buffer. Fluorescent output is measured immediately following compound addition (12.5 μl/well) on the FLIPR machine.

An $EC_{50}$ value was calculated using the change of fluorescent intensity from the reaction initiation. In general, compounds provided herein have $EC_{50}$ values of 5 μM or less, for example from 0.001 μM to 5 μM. In some examples, compounds provided herein have $EC_{50}$ values from 0.1 μM to 5 μM, while in other examples from 0.5 μM to 5 μM. In other examples, compounds provided herein have $EC_{50}$ values of 2 μM or less; for example from 0.001 μM to 2 μM. Table 1 also contains the range in which the $EC_{50}$ for each corresponding compound occurs.: +indicates an $EC_{50}$ range from 0.001 μM to 0.1 μM; ++ indicates an $EC_{50}$ range between 0.1 μM and 0.25 μM; +++ indicates an $EC_{50}$ range from 0.25 μM to 0.50 μM; ++++ indicates an $EC_{50}$ range between 0.50 μM and 1.0 μM; +++++ indicates an $EC_{50}$ range from 1.0 μM to 5.0 μM, and ++++++ indicates an $EC_{50}$ greater than 5.0 μM.

Certain Assay Results

Various compounds of Formula (I) in free form or in pharmaceutically acceptable salt form, exhibit pharmacological properties, for example, as indicated by the in vitro tests described in this application. The $EC_{50}$ value in those experiments is given as that concentration of the test compound in question that provoke a response halfway between the baseline and maximum responses. In certain examples compounds of Formula (I) have $EC_{50}$ values from 0.001 μM to 5 μM. In other examples, compounds of Formula (I) have $EC_{50}$ values from 0.001 μM to 4 μM. In other examples, compounds of Formula (I) have $EC_{50}$ values from 0.001 μM to 3 μM. In other examples, compounds of Formula (I) have $EC_{50}$ values from 0.001 μM to 2 μM. In other examples, compounds of Formula (I) have $EC_{50}$ values from 0.001 μM to 1 μM. In other examples, compounds of Formula (I) have $EC_{50}$ values from 0.001 μM to 0.5 μM. In other examples, compounds of Formula (I) have $EC_{50}$ values from 0.001 μM to 0.25 μM. In other examples, compounds of Formula (I) have $EC_{50}$ values from 0.001 μM to 0.1 μM.

Various compounds of Formula (I) in free form or in pharmaceutically acceptable salt form, exhibit pharmacological properties, for example, as indicated by the in vitro tests described in this application. The % efficiency in those experiments is given as that % enhancement of the test compound in question relative to a known compound. In certain examples compounds of Formula (I) have a % efficiency values from 50% to 150%. In other examples, compounds of Formula (I) have a % efficiency values from 55% to 150%. In other examples, compounds of Formula (I) have a % efficiency values from 60% to 150%. In other examples, compounds of Formula (I) have a % efficiency values from 65% to 150%. In other examples, compounds of Formula (I) have a % efficiency values from 70% to 150%. In other examples, compounds of Formula (I) have a % efficiency values from 75% to 150%. In other examples, compounds of Formula (I) have a % efficiency values from 80% to 150%. In other examples, compounds of Formula (I) have a % efficiency values from 85% to 150%. In other examples, compounds of Formula (I) have a % efficiency values from 90% to 150%. In other examples, compounds of Formula (I) have a % efficiency values from 95% to 150%. In other examples, compounds of Formula (I) have a % efficiency values from 100% to 150%.

By way of example only, the $EC_{50}$ for GPR120 activation by certain compounds of Formula (I) are listed in Table 2 below. The identifying number for each compound is the compound number from Table 1.

TABLE 2

| Compound Number | $EC_{50}$ (μM) | % Efficiency |
|---|---|---|
| 2 | 0.396 | 102 |
| 3 | 0.547 | 85.6 |
| 6 | 0.541 | 123 |
| 7 | 0.109 | 124 |
| 8 | 0.780 | 88.1 |
| 9 | 0.207 | 98.4 |
| 10 | 0.485 | 86.2 |
| 16 | 0.479 | 96.9 |
| 19 | 0.628 | 81.1 |
| 20 | 0.119 | 77.1 |
| 21 | 0.446 | 84.7 |
| 24 | 0.184 | 71.2 |
| 27 | 0.7 | 65.9 |
| 31 | 0.078 | 114 |
| 40 | 0.354 | 107 |
| 44 | 0.604 | 75.2 |
| 45 | 0.526 | 87.9 |
| 51 | 0.184 | 55 |
| 54 | 1.4 | 68.9 |
| 56 | 0.29 | 60.4 |
| 57 | 1.345 | 53.7 |
| 64 | 0.878 | 69 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for the purposes as stated.

We claim:

1. A compound of Formula (I):

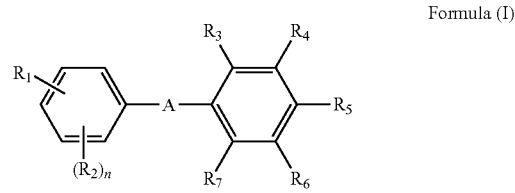

wherein:

n is selected from 0, 1, 2, 3 and 4;

A is:

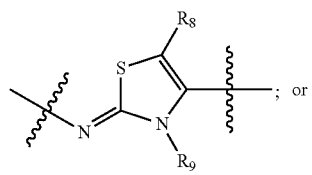

; or

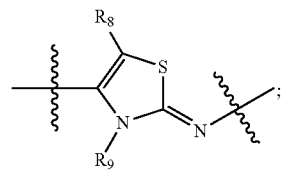

;

R$_8$ is selected from H, C$_{1-4}$alkyl and phenyl optionally substituted with 1 to 3 radicals independently selected from halo, C$_{1-4}$alkyl, halo-substitued-C$_{1-4}$-alkyl, C$_{1-4}$alkoxy and halo-substituted-C$_{1-4}$alkoxy;

R$_9$ is selected from C$_{1-6}$alkyl, halo-substitued-C$_{1-4}$alkyl and —X$_1$R$_{10}$; wherein X$_1$ is a bond or C$_{1-4}$alkylene; R$_{10}$ is C$_{3-8}$cycloalkyl;

R$_1$ is selected from —COOH, —SO$_3$H and tetrazolyl;

R$_2$ is selected from halo, C$_{1-4}$alkyl, halo-substituted-C$_{1-4}$alkyl, C$_{1-4}$alkoxy and halo-substituted-C$_{1-4}$alkoxy;

R$_3$, R$_4$, R$_5$, R$_6$ or R$_7$ are independently selected from H, cyano, hydroxyl, nitro, halo, C$_{1-4}$-alkyl, halo-substitued-C$_{1-4}$alkyl, C$_{1-4}$alkoxy, halo-substituted-C$_{1-4}$alkoxy, X$_2$OR$_{11}$, —X$_2$NR$_{12}$R$_{13}$, —X$_2$R$_{11}$, —X$_2$OX$_3$R$_{11}$ and —X$_2$OX$_3$OR$_{11}$; wherein X$_2$ is selected from a bond and C$_{1-4}$-alkylene; X$_3$ is C$_{1-4}$-alkylene; R$_{11}$ is selected from C$_{1-6}$alkyl, heteroaryl and aryl, each optionally substituted with 1 to 3 radicals independently selected from halo, cyano, hydroxyl, nitro, amino, C$_{1-4}$alkyl, halo-substitued-C$_{1-4}$alkyl, C$_{1-4}$-alkoxy and halo-substituted-C$_{1-4}$alkoxy; R$_{12}$ and R$_{13}$ are independently selected from H and C$_{1-6}$alkyl; or R$_3$ and R$_4$ or R$_5$ and R$_6$ are each independently C$_{1-4}$alkyl and taken together with the carbon atoms to which they are attached can form a phenyl ring; wherein said phenyl of the combination of R$_3$ and R$_4$ or R$_5$ and R$_6$ is optionally substituted with 1 to 3 radicals independently selected from cyano, amino, hydroxyl, nitro, halo, C$_{1-4}$alkyl, halo-substitued-C$_{1-4}$alkyl, C$_{1-4}$-alkoxy and halo-substituted-C$_{1-4}$alkoxy;

or the pharmaceutically acceptable salts thereof.

2. The compound of claim 1, wherein the compound of Formula (I) has a structure of Formula (Ia):

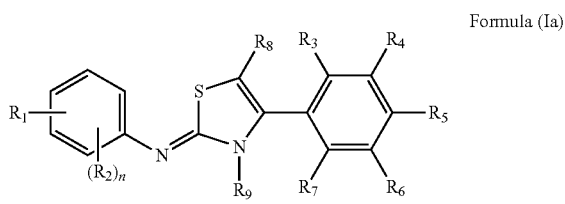

Formula (Ia)

wherein:

n is selected from 0, 1, 2, 3 and 4;

R$_8$ is selected from H, C$_{1-4}$-alkyl and phenyl optionally substituted with 1 to 3 radicals independently selected from halo, C$_{1-4}$-alkyl, halo-substituted-C$_{1-4}$alkyl, C$_{1-4}$alkoxy and halo-substituted-C$_{1-4}$alkoxy;

R$_9$ is selected from C$_{1-6}$alkyl, halo-substitued-C$_{1-4}$alkyl and —X$_1$R$_{10}$; wherein X$_1$ is a bond or C$_{1-4}$-alkylene; R$_{10}$ is C$_{3-8}$cycloalkyl;

R$_1$ is selected from —COOH, —SO$_3$H and tetrazolyl;

each R$_2$ is independently selected from halo, C$_{1-4}$-alkyl, halo-substituted-C$_{1-4}$-alkyl, C$_{1-4}$alkoxy and halo-substituted-C$_{1-4}$alkoxy;

R$_3$, R$_4$, R$_5$, R$_6$ or R$_7$ are independently selected from H, cyano, hydroxyl, nitro, halo, C$_{1-4}$-alkyl, halo-substitued-C$_{1-4}$alkyl, C$_{1-4}$alkoxy, halo-substituted-C$_{1-4}$-alkoxy, X$_2$OR$_{11}$, —X$_2$NR$_{12}$R$_{13}$, —X$_2$R$_{11}$, —X$_2$OX$_3$R$_{11}$ and —X$_2$OX$_3$OR$_{11}$; wherein X$_2$ is selected from a bond and C$_{1-4}$-alkylene; X$_3$ is C$_{1-4}$alkylene; R$_{11}$ is selected from C$_{1-6}$alkyl, heteroaryl and aryl, each optionally substituted with 1 to 3 radicals independently selected from halo, cyano, hydroxyl, nitro, amino, C$_{1-4}$alkyl, halo-substitued-C$_{1-4}$-alkyl, C$_{1-4}$-alkoxy and halo-substituted-C$_{1-4}$ alkoxy; R$_{12}$ and R$_{13}$ are independently selected from H and C$_{1-6}$alkyl; or R$_3$ and R$_4$ or R$_5$ and R$_6$ are each independently C$_{1-4}$alkyl and taken together with the carbon atoms to which they are attached can form a phenyl ring; wherein said phenyl of the combination of R$_3$ and R$_4$ or R$_5$ and R$_6$ is optionally substituted with 1 to 3 radicals independently selected from cyano, amino, hydroxyl, nitro, halo, C$_{1-4}$alkyl, halo-substitued-C$_{1-4}$-alkyl, C$_{1-4}$-alkoxy and halo-substituted-C$_{1-4}$-alkoxy;

or the pharmaceutically acceptable salts thereof.

3. The compound of claim 2, wherein R$_8$ is H or C$_{1-4}$alkyl.

4. The compound of claim 3, wherein each R$_2$ is independently a halo.

5. The compound of claim 4, wherein each R$_2$ is independently selected from fluoro and bromo.

6. The compound of claim 1 selected from:

(Z)-4-(4-(3-cyanophenyl)-3-ethylthiazol-2(3H)-ylideneamino)benzenesulfonic acid, (Z)-4-(4-(3,5-bis(trifluoromethyl)phenyl)-3-ethylthiazol-2(3H)-ylideneamino)benzenesulfonic acid, (Z)-4-(3-ethyl-5-methyl-4-phenylthiazol-2(3H)-ylideneamino)benzenesulfonic acid, (Z)-4-(3-ethyl-4-(3-fluorophenyl)thiazol-2(3H)-ylideneamino)benzenesulfonic acid, (Z)-4-(4-(3-bromophenyl)-3-ethylthiazol-2(3H)-ylideneamino)benzenesulfonic acid, (Z)-4-(3-ethyl-4-(2-(trifluoromethoxy)phenyl)thiazol-2(3H)-ylideneamino)benzenesulfonic acid, (Z)-4-(4-(2,5-dichlorophenyl)-3-ethylthiazol-2(3H)-ylideneamino)benzenesulfonic acid, (Z)-4-(3-ethyl-4-(2-phenoxyphenyl)thiazol-2(3H)-ylideneamino)benzoic acid, (Z)—N-(3-ethyl-4-phenylthiazol-2(3H)-ylidene)-4-(2H-tetrazol-5-yl)aniline, (Z)-4-(3-ethyl-4-phenylthiazol-2(3H)-ylideneamino)-2,3-difluorobenzoic acid, (Z)-4-(3-ethyl-4-(2-(trifluoromethyl)phenyl)thiazol-2(3H)-ylideneamino)benzoic acid, (Z)-4-(3-ethyl-4-(2-(trifluoromethoxy)phenyl)thiazol-2(3H)-ylideneamino)benzoic acid, (Z)-4-(3-ethyl-4-(3-(trifluoromethoxy)phenyl)thiazol-2(3H)-ylideneamino)benzoic acid, (Z)-4-(3-ethyl-4-phenylthiazol-2(3H)-ylideneamino)-2-fluorobenzoic acid, (Z)-2-bromo-4-(3-ethyl-4-phenylthiazol-2(3H)-ylideneamino)benzoic acid, (Z)-4-(4-phenyl-3-propylthiazol-2(3H)-ylideneamino)benzoic acid, (Z)-4-(3-isopropyl-4-phenylthiazol-2(3H)-ylideneamino)benzoic acid, (Z)-4-(3-ethyl-4-(3-hydroxyphenyl)thiazol-2(3H)-ylideneamino)benzoic acid, (Z)-4-(4-(2-bromo-5-hydroxyphenyl)-3-ethylthiazol-2(3H)-ylideneamino)benzoic acid, (Z)-4-(3-ethyl-4-(3-(2-methoxyethoxy)phenyl)thiazol-2(3H)-ylideneamino)benzoic acid, (Z)-4-(3-(cyclopropylmethyl)-4-phenylthiazol-2(3H)-ylideneamino)benzoic acid, (Z)-4-(3-sec-butyl-4-phenylthiazol-2(3H)-ylideneamino)benzoic acid, (Z)-4-(3-(2,2-difluoroethyl)-4-phenylthiazol-2(3H)-ylideneamino)benzoic acid, (Z)-4-(4-phenyl-3-(2,2,2-trifluoroethyl)thiazol-2(3H)-ylideneamino)benzoic acid,
(Z)-4-(3-ethyl-4-phenylthiazol-2(3H)-ylideneamino)-2,3,5,6-tetrafluorobenzoic acid,
(Z)-4-(4-(3-(benzyloxy)phenyl)-3-ethylthiazol-2(3H)-ylideneamino)benzoic acid,
(Z)-4-(3-ethyl-4-(3-(pyridin-2-ylmethoxy)phenyl)thiazol-2(3H)-ylideneamino)benzoic acid,
(Z)-4-(3-ethyl-4-(2-methoxyphenyl)thiazol-2(3H)-ylideneamino)benzenesulfonic acid,
(Z)-4-(3-ethyl-4-(3-methoxyphenyl)thiazol-2(3H)-ylideneamino)benzenesulfonic acid,
(Z)-4-(4-(2-chlorophenyl)-3-ethylthiazol-2(3H)-ylideneamino)benzenesulfonic acid,
(Z)-4-(4-(3-chlorophenyl)-3-ethylthiazol-2(3H)-ylideneamino)benzenesulfonic acid
(Z)-4-(3-ethyl-4-(2-methoxyphenyl)thiazol-2(3H)-ylideneamino)benzoic acid,
(Z)-4-(3-ethyl-4-(3-methoxyphenyl)thiazol-2(3H)-ylideneamino)benzoic acid,
(Z)-4-(4-(2-chlorophenyl)-3-ethylthiazol-2(3H)-ylideneamino)benzoic acid,
(Z)-4-(4-(3-chlorophenyl)-3-ethylthiazol-2(3H)-ylideneamino)benzoic acid,
(Z)-4-(3-ethyl-4-phenylthiazol-2(3H)-ylideneamino)benzoic acid,
(Z)-4-(3-ethyl-4-phenylthiazol-2(3H)-ylideneamino)benzenesulfonic acid,
(Z)-4-(4-(2,6-dichlorophenyl)-3-ethylthiazol-2(3H)-ylideneamino)benzoic acid,
(Z)-4-(4-(2,3-dichlorophenyl)-3-ethylthiazol-2(3H)-ylideneamino)benzoic acid,
(Z)-4-(3-ethyl-4-(naphthalen-1-yl)thiazol-2(3H)-ylideneamino)benzoic acid,
(Z)-4-(3-ethyl-4-(naphthalen-2-yl)thiazol-2(3H)-ylideneamino)benzoic acid,
(Z)-4-(4-(2-bromophenyl)-3-ethylthiazol-2(3H)-ylideneamino)benzoic acid,
(Z)-4-(4-(2-aminophenyl)-3-ethylthiazol-2(3H)-ylideneamino)benzoic acid,
(Z)-4-(3-ethyl-4-(2-nitrophenyl)thiazol-2(3H)-ylideneamino)benzoic acid,
(Z)-4-(3-ethyl-4-(2-(methylamino)phenyl)thiazol-2(3H)-ylideneamino)benzoic acid,
(Z)-4-(4-(2-(dimethylamino)phenyl)-3-ethylthiazol-2(3H)-ylideneamino)benzoic acid,
(Z)-4-(4-(3-bromophenyl)-3-ethylthiazol-2(3H)-ylideneamino)benzoic acid,
(Z)-4-(3-ethyl-4-(2-hydroxyphenyl)thiazol-2(3H)-ylideneamino)benzoic acid,
(Z)-4-(4-(3-cyanophenyl)-3-ethylthiazol-2(3H)-ylideneamino)benzoic acid, and
(Z)-4-(4-(5-bromo-2-hydroxyphenyl)-3-ethylthiazol-2(3H)-ylideneamino)benzoic acid.

7. A pharmaceutical composition comprising a therapeutically effective amount of a compound of Formula (I) of claim 1, and a pharmaceutically acceptable carrier.

8. A method for treating a disease or disorder where modulation of GPR120 is implicated, comprising administering to a system or subject in need of such treatment an effective amount of a compound of Formula (I) of claim 1, or pharmaceutically acceptable salts or pharmaceutical compositions thereof, thereby treating the disease or disorder wherein the disease or disorder is selected from diabetes, obesity, diabetes mellitus, dyslipidemia, hyperlipidemia, anorexia, hyperphagia, endocrine abnormalities, and triglyceride storage disease.

9. The method of claim 8, wherein the system or subject is a cell or tissue system; or a human or animal subject.

10. The method of claim 8, wherein the disease or disorder is an autoimmune disease wherein the autoimmune disease is rheumatoid arthritis, systemic lupus erythematosus, idiopathic thrombocytopenic purpura, hemolytic anemia, or psoriasis.

11. The method of any of claim 8, wherein the compound is an agonist of GPR120.

* * * * *